US010786475B2

(12) United States Patent
Lee

(10) Patent No.: US 10,786,475 B2
(45) Date of Patent: Sep. 29, 2020

(54) METHOD FOR PREVENTING, TREATING, OR IMPROVING FATTY LIVER BY ADMINISTERING EFFECTIVE AMOUNTS OF AZELAIC ACID TO A SUBJECT

(71) Applicant: Korea University Research and Business Foundation, Seoul (KR)

(72) Inventor: Sung-Joon Lee, Seoul (KR)

(73) Assignee: Korea University Research and Business Foundation, Seoul (KR)

( * ) Notice: Subject to any disclaimer, the term of this patent is extended or adjusted under 35 U.S.C. 154(b) by 0 days.

(21) Appl. No.: 16/279,015

(22) Filed: Feb. 19, 2019

(65) Prior Publication Data
US 2019/0255006 A1  Aug. 22, 2019

(30) Foreign Application Priority Data

Feb. 20, 2018 (KR) .................. 10-2018-0020080
Feb. 19, 2019 (KR) .................. 10-2019-0019111

(51) Int. Cl.
*A61K 31/194* (2006.01)
*A61K 31/20* (2006.01)
*A61P 1/16* (2006.01)

(52) U.S. Cl.
CPC ............ *A61K 31/20* (2013.01); *A61P 1/16* (2018.01)

(58) Field of Classification Search
CPC .................................. A61K 31/194
USPC ..................................... 514/574
See application file for complete search history.

(56) References Cited

U.S. PATENT DOCUMENTS

2012/0251525 A1* 10/2012 Streeper ............... A61K 31/23
424/130.1

FOREIGN PATENT DOCUMENTS

| CN | 1192134 A | 9/1998 |
|---|---|---|
| KR | 10-2004-0010681 A | 1/2004 |
| KR | 10-2012-0064604 A | 6/2012 |
| KR | 10-2013-0101515 A | 9/2013 |
| KR | 10-2015-0028958 A | 3/2015 |

OTHER PUBLICATIONS

Wu, Chunyan et al., "Olfactory receptor 544 reduces adiposity by steering fuel preference toward fats", The Journal of Clinical Investigation, vol. 127, Issue 11 (12 pages in English).
United States Office Action dated May 6, 2019 in related application, U.S. Appl. No. 15/861,239 (24 pages in English).
United States Office Action dated Nov. 18, 2019 in related application, U.S. Appl. No. 15/861,239 (17 pages in English).
Thach et al., "Molecular determinants of the olfactory receptor Olfr544 activation by azelaic acid," Biochemical and Biophysical Research Communications, 485, Feb. 20, 2017, (pp. 241-248).
Muthulakshmi et al., "Protective effects of azelaic acid against high-fat diet-induced oxidative stress in liver, kidney and heart of C57BL/6J mice"; 2013; Mol Cell Biochem.; 377:23-33 (Year: 2013).
Deeks et al., "Rosiglitazone A Review of its Use in Type 2 Diabetes Mellitus," Drugs, 67:2747-2779 (2007).
Carmona et al., "Fenofibrate Prevents Rosiglitazone-Induced Body Weight Gain in ob/ob Mice," International Journal of Obesity, 29:864-871 (2005).
Chaput et al., "Fenofibrate and Rosiglitazone Lower Serum Triglycerides with Opposing Effects on Body Weight," Biochemical and Biophysical Research Communications, 271:445-450, 2000.
Kahn et al., "Glycemic Durability of Rosiglitazone, Metformin, or Glyburide Monotherapy," The New England Journal of Medicine, 2427-2443, Dec. 7, 2006.
Muthulakshmi et al., "Gene Expression Profile of High-Fat Diet-Fed C57BL/6J Mice: In Search of Potential Role of Azelaic Acid," J. Physiol. Biochem, 71 (2015) 29-42.
Wilson-Fritch et al., "Mitochondrial remodeling in adipose tissue associated with obesity and treatment with rosiglitazone," The Journal of Clinical Investigation, vol. 114, No. 9, Nov. 1, 2004, pp. 1281-1289.
Perreault et al., "PPAR-delta Agonism for the Treatment of Obesity and Associated Disorders: Challenges and Opportunities," PPAR Research, vol. 2008, Jan. 1, 2008, pp. 1-9.
Supplementary European Search Report, Application No. EP16821568.9; dated Jan. 29, 2019.
Zhuang et al., "Evaluating cell-surface expression and measuring activation of mammalian odorant receptors in heterologous cells," Nature Protocols, vol. 3, No. 9, pp. 1402-1413, Aug. 14, 2008.
Wu et al., "Activation of OR1A1 suppresses PPAR-$\gamma$ expression by inducing HES-1 in cultured hepatocytes," The International Journal of Biochemistry & Cell Biology, 64 (2015) 75-80.
Muthulakshmi et al., "Efficacy of azelaic acid on hepatic key enzymes of carbohydrate metabolism in high fat diet induced type 2 diabetic mice," Biochimie, vol. 95, No. 6 (Feb. 28, 2013), pp. 1239-1244, XP028593691.
Kang et al., "Olfactory receptor Olfr544 responding to azelaic acid regulates glucagon secretion in $\alpha$-cells of mouse pancreatic islets," Biochemical and Biophysical Research Communications, 460, No. 3 (Mar. 21, 2015) pp. 616-621, XP029156356.

(Continued)

Primary Examiner — Raymond J Henley, III
(74) Attorney, Agent, or Firm — NSIP Law

(57) ABSTRACT

A method for preventing, improving, or treating fatty liver includes administering an effective amount of an azelaic acid or a pharmaceutically acceptable salt thereof to a subject. Azelaic acid which is a compound primarily contained in a natural product, has no or fewer side effects and reduces accumulation of triglycerides in liver tissue, and thus may prevent, improve, or treat a non-alcoholic fatty liver. In addition, due to an anti-inflammatory effect, azelaic acid may be used in the treatment of steatohepatitis. Therefore, the azelaic acid according to the present disclosure is expected to be effectively used in a food composition, a pharmaceutical composition and a health functional food composition to treat fatty liver or steatohepatitis.

10 Claims, 22 Drawing Sheets
Specification includes a Sequence Listing.

(56) References Cited

OTHER PUBLICATIONS

Green et al, "An Established Preadipose Cell Line and its Differentiation in Culture," Cell, vol. 5, pp. 19-27 (May 1975).
Green et al, "An Established Pre-Adipose Cell Line and its Differentiation in Culture," Cell, vol. 3, pp. 127-133 (Oct. 1974).
Atanasov et al., "Honokiol: a non-adipogenic PPARγ agonist from nature", Biochimica et Biophysica Acta, 1830 (2013) pp. 4813-4819.
Zhang, Yi et al., "Progress of Preclinical Pharmaceutical Research on Azelaic Acid," China pharmaceutical Industry, vol. 16, No. 18, Sep. 20, 2007 (5 pages in English, 2 pages in Chinese).
Chinese Office Action dated Mar. 16, 2020 in Chinese Patent Application No. 201680045618.7 (6 pages in English, 5 pages in Chinese).

* cited by examiner

SEQUENCE LISTING

```
<160> NUMBER OF SEQ ID NOS: 2

<210> SEQ ID NO 1
<211> LENGTH: 51
<212> TYPE: DNA
<213> ORGANISM: Artificial Sequence
<220> FEATURE:
<223> OTHER INFORMATION: oligonucleotide encoding shRNA hairpin
      sequences targeting Olfr544

<400> SEQUENCE: 1
caccgctcac tgttcgcatc ttcattcgaa aatgaagatg cgaacagtga g         51

<210> SEQ ID NO 2
<211> LENGTH: 47
<212> TYPE: DNA
<213> ORGANISM: Artificial Sequence
<220> FEATURE:
<223> OTHER INFORMATION: oligonucleotide encoding non-targeting
      scrambled shRNA hairpins

<400> SEQUENCE: 2
caccgtaagg ctatgaagag ataccgaagt atctcttcat agcctta               47
```

METHOD FOR PREVENTING, TREATING, OR IMPROVING FATTY LIVER BY ADMINISTERING EFFECTIVE AMOUNTS OF AZELAIC ACID TO A SUBJECT

CROSS-REFERENCE TO RELATED APPLICATION

This application claims priority to and the benefit of Korean Patent Application No. 10-2018-0020080, filed on Feb. 20, 2018, and Korean Patent Application No. 10-2019-0019111, filed on Feb. 19, 2019, the disclosures of which are incorporated by reference in their entirety.

TECHNICAL FIELD

The following description relates to a method for preventing, improving or treating fatty liver by administering an effective amount of an azelaic acid to a subject.

BACKGROUND ART

Fatty liver is a condition that causes hypertrophy of the liver due to abnormal accumulation of triglycerides in liver cells. The main causes of fatty liver are excessive drinking, fatty liver, diabetes and hyperlipidemia, and the progression of fatty liver leads to hepatitis, cirrhosis and coronary atherosclerosis and may cause cardiovascular diseases such as myocardial infarction.

Fatty liver is classified into alcoholic fatty liver caused by excessive drinking and non-alcoholic fatty liver. Generally, the alcoholic fatty liver may be recovered from by avoiding drinking for several months. In the non-alcoholic fatty liver, it is important to control carbohydrate intake, but since Koreans consume rice as a staple food, it is not easy to reduce carbohydrate intake. Therefore, when a food-derived natural extract in a form of a pharmaceutical composition or a health functional food, which stimulates lipolysis in the liver, is applied together with dietary control, it may be effective in improving the fatty liver condition.

Olfactory receptor 544 (Olfr544) is one of G-protein coupled receptors (GPCRs) primarily expressed in adipose and liver tissues, and is a representative example of olfactory receptors, which perform various functions as ectopically expressed in various tissues, including delivery of odor information from olfactory epithelial cells to the cerebrum. Recent studies on olfactory receptors expressed in general tissues showed that mouse olfactory receptor family 174 (MPOR174) is involved in mobility and chemotaxis in sperm, and confirmed that mouse olfactory receptor family 23 (MOR23) is involved in regeneration of myocytes and migration in mouse muscle cells. In addition, Pluznick et al. confirmed that an olfactory receptor expressed in the mouse kidney, that is, olfactory receptor 78 (Olfr78) controls renin secretion and blood pressure in response to a short-chain fatty acid. This suggests that the olfactory receptor has other functions than those previously known.

Azelaic acid (AzA) is an organic compound which is primarily contained in grains such as wheat, oats, barley, sorghum and rye, and foods such as cranberries, and has two carboxyl groups in one molecule. As known to date, AzA has therapeutic efficacy on inflammatory skin diseases such as acne, flushing, and the like, and some studies on arteriosclerosis and an anti-cancer effect have been reported. However, detailed mechanisms thereof are not known yet.

Under the above technical circumstances, the inventors confirmed that AzA acts as an Olfr544 ligand in the liver and stimulates decomposition of triglycerides through a PKA-CREB signaling pathway, thereby having a fatty liver improving effect.

PRIOR ART DOCUMENT

Patent Document

Korean Unexamined Patent Application Publication No. 10-20150028958

DISCLOSURE

Technical Problem

The following description is directed to a pharmaceutical composition for preventing or treating fatty liver, and a food composition for preventing or improving fatty liver, which includes an effective amount of an AzA or a pharmaceutically acceptable salt thereof as an active ingredient.

The following description is also directed to a method for preventing, improving or treating fatty liver, which includes administering an effective amount of an AzA or a pharmaceutical acceptable salt thereof to a subject in need thereof.

However, technical problems to be solved in the present disclosure are not limited to the above-described problems, and other problems which are not described herein will be fully understood by those of ordinary skill in the art from the following descriptions.

Technical Solution

To solve the above-described technical problems, the following description provides a pharmaceutical composition for preventing, improving, or treating fatty liver, which includes an effective amount of an AzA or a pharmaceutically acceptable salt thereof as an active ingredient, and a method for preventing, improving or treating fatty liver, which includes administering the composition to a subject.

In addition, the following description provides a food composition for preventing, improving, or treating fatty liver, which includes an effective amount of an AzA or a pharmaceutically acceptable salt thereof as an active ingredient, and a method for preventing, improving, or treating fatty liver, which includes administering the composition to a subject.

In one exemplary embodiment, the composition or the method may enable an activation of Olfr544 in liver tissue.

In another exemplary embodiment, the composition or the method may enable an activation of PPARα in liver tissue.

In still another exemplary embodiment, the composition or the method may enable an inhibition of an accumulation of triglycerides in liver tissue.

In yet another exemplary embodiment, the composition or the method may enable an inhibition of an accumulation of triglycerides in liver tissue by sequentially activating cAMP-PKA-CREB-PPARα through Olfr544 activation.

In yet another exemplary embodiment, the fatty liver may be a non-alcoholic fatty liver.

In yet another exemplary embodiment, the fatty liver may be steatohepatitis caused by a deposition of fat and inflammation in hepatocytes.

In addition, the following description provides a method for preventing, improving, or treating fatty liver, which includes administering an effective amount of an AzA or a pharmaceutically acceptable salt thereof to a subject.

In addition, the following description provides a method for preparing a drug for preventing, improving, or treating fatty liver, which includes preparing an effective amount of an AzA or a pharmaceutically acceptable salt thereof.

Advantageous Effects

It has been confirmed that the AzA according to the present disclosure is a compound usually contained in grains such as wheat, oats, barley, sorghum and rye, and a natural product such as cranberries, has no or fewer side effects, and is effective in reducing a degree of accumulating triglycerides in liver tissue, and thus can be used in treatment and improvement of a non-alcoholic fatty liver. In addition, an anti-inflammatory effect of the AzA in a liver-derived cell line was confirmed, and thus the AzA can be used in the treatment of steatohepatitis.

Therefore, the AzA according to the present disclosure can be effectively used for a food material, a drug composition or a health functional food for treating fatty liver or a steatohepatitis.

DESCRIPTION OF DRAWINGS

FIG. 2A shows the increase in cAMP and PKA activities, FIG. 2B shows the increase in p-CREB protein expression, FIG. 2C shows an Olfr544 knockdown effect in response to the Olfr544 shRNA treatment and the change in p-CREB protein expression in the AzA-treated group.

FIG. 4A shows an inhibition of a body weight gain after the 6-week oral administration of the AzA in a wild-type mouse (WT) and an Olfr544 KO mouse, FIG. 4B shows the reduction of triglycerides in a liver tissue, FIG. 4C shows the increase in PPARα downstream gene expression in a liver, FIG. 4D shows the increase in a fatty acid oxidation rate, FIG. 4E shows the change in an energy metabolism through an indirect calorimetric assay.

FIG. 5A shows an inhibition of the increase in body weight after 6-week oral administration of the AzA in ob/ob mice, FIG. 5B shows the reduction of triglycerides in liver tissue, and FIG. 5C shows the increase in PPARα downstream gene expression in the liver. In addition.

FIG. 7A shows the activity of GPCR-dependent transcription factors of a cAMP/PKA pathway, a calcium/PKC pathway, a ERK and JNK signal transduction, an I-3 kinase/AKT pathway, a MEF2 pathway, a Hedgehog pathway, a NF-kB pathway and a JAK/STAT pathway in Hepa1c1c-7 cells stimulated by LPS, and FIGS. 7B and 7C show the analyses of IL-6 and TNFα mRNA gene expression, and IL-6 and TNFα cytokine concentrations.

FIG. 8A shows the activity of GPCR-dependent transcription factors of a cAMP/PKA pathway, a calcium/PKC pathway, a ERK and JNK signal transduction, a I-3 Kinase/AKT pathway, a MEF2 pathway, a Hedgehog pathway, a NF-kB pathway, and a JAK/STAT pathway in 3T3-L1 cells stimulated by LPS, and FIG. 8B shows IL-6 and TNFα mRNA gene expression.

MODES OF THE DISCLOSURE

Figure 1:
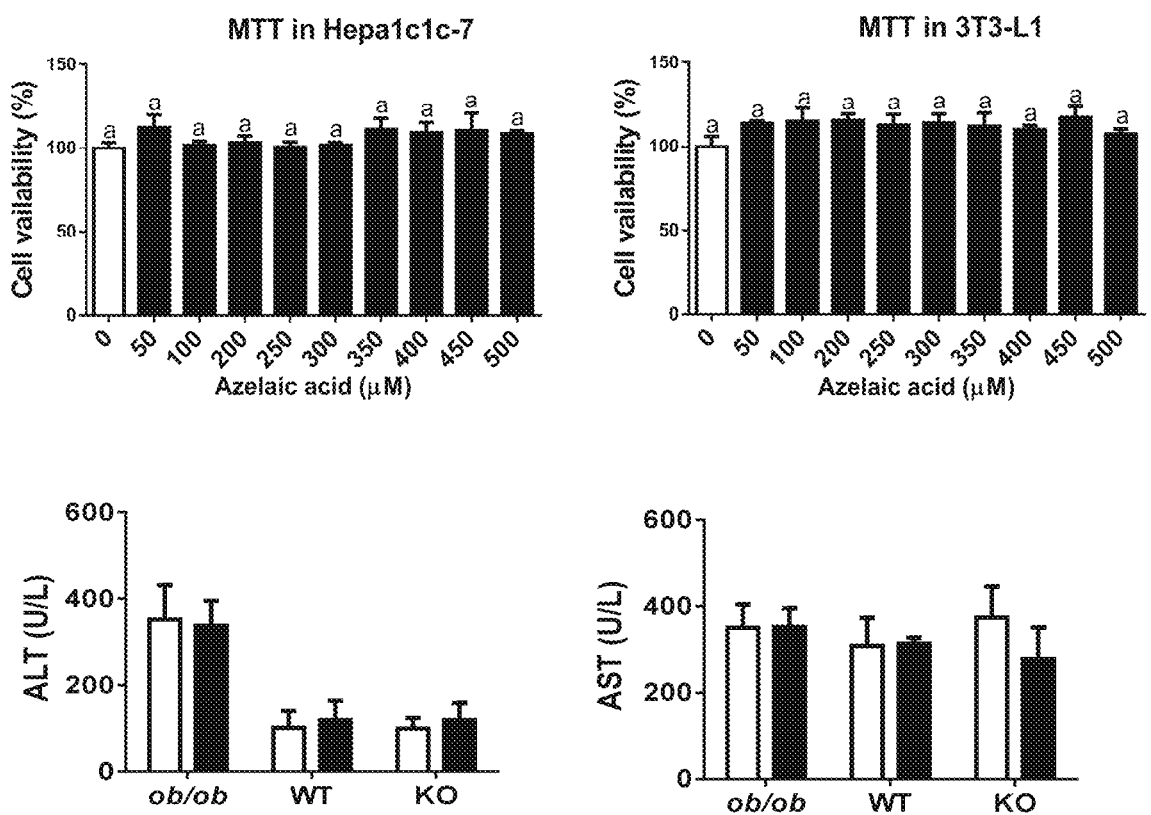
FIG. 1 is a set of graphs for evaluating cytotoxicity of the AzA using an MTT assay.

Exemplary embodiments of the present disclosure will be described in detail below with reference to the accompanying drawings. While the present disclosure is shown and described in connection with exemplary embodiments thereof, it will be apparent to those skilled in the art that various modifications can be made without departing from the spirit and scope of the claimed invention.

The inventors confirmed that an AzA primarily contained in grains such as wheat, oats, barley, sorghum and rye and a natural product such as cranberries inhibits the accumulation of triglycerides in a liver tissue-derived cell line, and through a further study, also confirmed that an AzA acts as a ligand of a G-protein coupled receptor (GPCR), that is, olfactory receptor 544 (Olfr544), in hepatocytes and inhibits the accumulation of triglycerides in a liver tissue by activating an Olfr544-cAMP-protein kinase A (PKA)-cAMP response element binding protein (CREB)-peroxisome proliferator-activated receptor α (PPARα) pathway.

The present disclosure provides a composition for preventing, improving, or treating fatty liver, which includes an effective amount of an AzA or a pharmaceutically acceptable salt thereof, and a method for preventing, improving, or treating fatty liver, which includes administering the composition to a subject.

The term "azelaic acid (AzA)" refers to nonanedioic acid, and has a structure of Formula 1 with a molecular weight of 188.22 g/mol and a molecular formula of $C_9H_{16}O_4$.

[Formula 1]

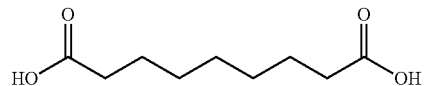

An AzA is a compound, which is primarily contained in grains such as wheat, oats, barley, sorghum and rye, and foods such as cranberries, and has no or fewer side effects when being administered to a subject. In one exemplary embodiment, as a result of evaluating the cytotoxicity of an AzA through an MTT assay, it was shown that, even when a high concentration of the AzA is treated, there is almost no change in cell viability, reconfirming the stability of the AzA (see Example 1).

Since the AzA of the present disclosure is a natural substance and thus has no toxicity, it can be continuously used as an active ingredient of a food or medicine in great quantities.

The AzA of the present disclosure may be obtained from grains such as wheat, oats, barley, sorghum and rye and a natural product such as cranberries through a conventional extraction method such as juice extraction, vapor extraction, hot-water extraction, ultrasonic extraction, solvent extraction or reflux extraction. For example, for the extraction, one or more solvents selected from the group consisting of water, an alcohol having 1 to 4 carbon atoms, n-hexane, ethyl acetate, acetone, butyl acetate, 1,3-butylene glycol, methylene chloride and a mixture thereof may be used, but the present disclosure is not limited thereto.

In addition, the AzA of the present disclosure may be a synthetic compound, but such an AzA has the same efficacy as obtained from a natural product and can be used for the same purpose thereof.

The AzA of the present disclosure may be used in the form of a pharmaceutically acceptable salt, and as a salt, an acid-addition salt formed by a pharmaceutically acceptable free acid is preferable.

The term "salt" used herein is preferably an acid-addition salt formed by a pharmaceutically acceptable free acid. The acid-addition salt is obtained from an inorganic acid such as hydrochloric acid, nitric acid, phosphoric acid, sulfonic acid, hydrobromic acid, hydroiodic acid, nitrous acid or phosphorous acid; an aliphatic mono or dicarboxylate, a phenyl-substituted alkanoate, hydroxy alkanoate or alkandioate, an aromatic acid, or a non-toxic organic acid such as an aliphatic or aromatic sulfonic acid. Such pharmaceutically non-toxic salts include sulfates, pyrosulfates, bisulfates, sulfites, bisulfites, nitrates, phosphates, monohydrogen phosphates, dihydrogen phosphates, metaphosphates, pyrophosphates, chlorides, bromides, iodides, fluorides, acetates, propionates, decanoates, caprylates, acrylates, formates, isobutyrates, caprates, heptanoates, propiolates, oxalates, malonates, succinates, suberates, sebacates, fumarates, maleates, butyne-1,4-dioates, hexane-1,6-dioates, benzoates, chlorobenzoates, methyl benzoates, dinitrobenzoates, hydroxy benzoates, methoxy benzoates, phthalates, terephthalates, benzene sulfonates, toluenesulfonates, chlorobenzene sulfonates, xylene sulfonates, phenylacetates, phenylpropionates, phenylbutyrates, citrates, lactates, β-hydroxybutyrates, glycolates, malates, tartrates, methanesulfonates, propane sulfonates, naphthalene-1-sulfonates, naphthalene-2-sulfonates, or mandelates.

The acid-addition salt according to the present disclosure may be prepared by a conventional method, for example, dissolving a compound represented by Formula 1 in an excessive amount of an acidic aqueous solution, and precipitating the salt using a water-miscible organic solvent, for example, methanol, ethanol, acetone or acetonitrile. Alternatively, the acid-addition salt according to the present disclosure may be prepared by evaporating the solvent or an excessive amount of acid from the mixture and then drying the resulting product, or suction-filtering the precipitated salt.

In addition, a pharmaceutically acceptable metal salt may be prepared using a base. An alkali metal or alkaline earth metal salt is obtained, for example, by dissolving the compound in an excessive amount of an alkali metal hydroxide or alkaline earth metal hydroxide solution, filtering a non-soluble compound salt, and evaporating and drying the filtrate. Here, as a metal salt, a sodium, potassium or calcium salt is preferable. The corresponding silver salt is obtained by reacting an alkali metal or alkaline earth metal with a suitable silver salt (e.g., silver nitrate).

In addition, the compound of the present disclosure includes all salts, isomers, hydrates and solvates, which can be prepared by conventional methods, as well as the pharmaceutically acceptable salt.

In addition, the composition of the present disclosure may include AzA as an active ingredient, and further include one or more types of materials conventionally used to prevent or treat fatty liver. For example, the composition may be prepared together with a drug such as an antihistamine drug, an anti-inflammatory analgesic drug, an anticancer agent, and/or an antibiotic, or may be used in combination thereof.

The "fatty liver" used herein refers to excessive accumulation of fats present in liver tissue due to excessive ingestion of fats, increase in fat synthesis in the liver or decrease in the excretion of fats. Generally, when cell damage occurs due to the accumulation of fats present in the liver, it is called a fatty liver, but the present disclosure is not limited thereto.

Fatty liver is broadly classified into alcoholic fatty liver and non-alcoholic fatty liver, and the alcoholic fatty liver is caused by a reduction of alcoholic metabolism efficiency in the liver due to excessive drinking, and thus has been known to be prevented, treated or improved by stopping the consumption of alcohol, and non-alcoholic fatty liver (NAFL) refers to a disease caused by the accumulation of triglycerides in the liver regardless of alcohol consumption.

Therefore, fatty liver disease to be prevented, treated or improved in the present disclosure is any type without limitation if fats are excessively accumulated in hepatocytes, and preferably, NAFL. In an exemplary embodiment, as a result of treatment of a mouse liver tissue-derived cell line, that is, Hepa1c1c7 cells, with the AzA, increase in cAMP and calcium concentrations in cells, increases in Olfr544 activity and PKA activity, and increase in p-CREB/CREB ratio were confirmed, compared with a control group, suggesting that the AzA serves as an Olfr544 ligand in hepatocytes to activate a cAMP-PKA-CREB signal transduction mechanism (see Example 2).

In addition, in an exemplary embodiment, as a result of treatment of Hepa1c1c 7 cells with the AzA, it was confirmed that PPARα expression and activity are increased and a fatty acid oxidation rate is increased, compared with a control group, (see Example 3), and as a result of the analysis of a triglyceride content in a liver tissue after 50 mg/kg of the AzA is orally administered into a fatty liver-induced mouse for 6 weeks, it was observed that a triglyceride concentration in the liver tissue is significantly decreased in an AzA-treated group, and it was confirmed through indirect calorimetric analysis that the AzA administration stimulates fatty acid oxidation in a mouse, thereby alleviating symptoms of NAFL, and after long-term administration of the AzA in HFD, WT and KO mice, a blood glycerol concentration, a body fat level, and insulin sensitivity were compared (see Example 4).

In addition, in an exemplary embodiment, after the AzA is orally administered into an obese mouse model, which is an ob/ob mouse, for 6 weeks, the NAFL improving effect of an AzA was reconfirmed in an obese model through analysis of hepatic triglycerides and the expression of the fat oxidation regulatory gene PPARα and a downstream gene thereof, and the liver tissue lipolytic effect of an AzA was reconfirmed in mouse primary hepatocytes (see Example 5).

In addition, in mice fed HFD, AzA- and barley-added diets, a body weight, a blood glucose, a blood glycerol concentration, and a cholesterol concentration were compared, showing that, compared with the barley-added diets group, in the AzA-added diets group, a body weight, an LDL cholesterol concentration, an ALT concentration, and a liver tissue triglyceride concentration are significantly decreased, and generally, compared with the barley-added diets having a fatty liver-alleviating effect, the AzA-added diets exhibits a superior effect (see Example 6).

In other words, in the present disclosure, the treatment of fatty liver is characterized by a reduction of triglycerides in blood and liver tissue and inhibition of fat accumulation in liver tissue, and the AzA may act on olfactory receptors, and particularly, an olfactory receptor expressed in liver tissue, that is, Olfr544, to activate the action of PPARα and stimulate fatty acid oxidation.

Meanwhile, NAFL includes simple steatosis and non-alcoholic steatohepatitis (NASH). The simple steatosis is considered as a benign disease which has a good prognosis clinically, but NASH is a progressive liver disease, which is a progressive disease that causes cirrhosis or liver cancer and needs a suitable treatment in a timely manner.

In an exemplary embodiment, the triglycerides accumulation-inhibitory effect of an AzA in liver tissue and the anti-inflammatory activity of the AzA were confirmed. More specifically, expression of inflammatory cytokines IL-6 and TNF-α is decreased according to the treatment of a liver tissue-derived cell line with AzA, demonstrating that inflammation can be effectively decreased by treating hepatocytes with the AzA (see Examples 7 to 9). Therefore, the composition of the present disclosure may be used as a composition for preventing, improving, or treating hepatitis as well as treating fatty liver, and particularly, may be used as a composition for preventing, improving, or treating steatohepatitis accompanying fatty liver caused by fat accumulation in liver tissue and inflammation.

The "prevention" used herein refers to all actions of inhibiting fat accumulation in liver tissue or delaying the onset of fatty liver by administering the composition according to the present disclosure, the "treatment" used herein refers to all actions involved in alleviating or beneficially changing symptoms of fatty liver by administering the composition according to the present disclosure, and the "improvement" used herein refers to all actions that reduce parameters associated with a fatty liver disease, for example, a severity of a symptom, by administering the composition according to the present disclosure.

In the present disclosure, the improvement of the fatty liver may be characterized by the decomposition and the inhibition of accumulation of triglycerides in liver tissue and the improvement of vascular health according thereto.

In the present disclosure, the pharmaceutical composition may further include suitable carrier, excipient and diluent, which are conventionally used in the preparation of a pharmaceutical composition.

The term "carrier" used herein is also called a vehicle, and means a compound that facilitates the addition of a compound into cells or tissue. For example, dimethyl sulfoxide (DMSO) is a carrier conventionally used to facilitate the input of various organic compounds into cells or tissue of an organism.

The term "diluent" used herein is defined not only as a compound which stabilizes a biologically active form of a target compound, but also as a compound which is diluted in a water dissolving the target compound. A salt dissolved in a buffer is used as a diluent in the art. A conventionally used buffer is phosphate buffered saline, and this is because it imitates a salt state of a human solution. Since the buffer salt can control the pH of a solution at a low concentration, the buffer diluent rarely modifies a biological activity of a compound. Compounds containing an AzA, which are used herein, may be administered to a human patient by themselves, or in the form of a pharmaceutical composition in combination with other components or a suitable carrier or excipient, as used in combination therapy.

In addition, the pharmaceutical composition for preventing, improving, or treating fatty liver, which includes an AzA, may be used in the form of a powder, a granule, a tablet, a capsule, a suspension, an emulsion, a syrup, an agent for external use, for example, an aerosol, or a sterile injection according to a conventional method, and carriers, excipients and diluents which can be included in the composition including an AzA may be lactose, dextrose, sucrose, oligosaccharide, sorbitol, mannitol, xylitol, erythritol, maltitol, starch, acacia gum, alginate, gelatin, calcium phosphate, calcium silicate, cellulose, methyl cellulose, microcrystalline cellulose, polyvinyl pyrrolidone, water, methyl hydroxybenzoate, propyl hydroxybenzoate, talc, magnesium stearate and mineral oil. The composition of the present disclosure may be formulated using a diluent or an excipient such as a filler, a thickening agent, a binder, a wetting agent, a disintegrant or a surfactant, which is conventionally used. A solid formulation for oral administration may be a tablet, a pill, a powder, a granule or a capsule, and such a solid formulation may be prepared by mixing at least one excipient, for example, starch, calcium carbonate, sucrose, lactose and gelatin, with the active ingredient. Also, in addition to the simple excipient, lubricants such as magnesium stearate and talc may also be used. A liquid formulation for oral administration may be prepared in the form of a suspension, a liquid for internal use, an emulsion or a syrup, and may include various types of excipients, for example, a wetting agent, a sweetener, a fragrance and a preservative as well as conventionally-used simple diluents such as water and liquid paraffin. A formulation for parenteral administration includes a sterilized aqueous solution, a non-aqueous solvent, a suspension, an emulsion, a lyophilizing agent and a suppository. As the non-aqueous solvent or suspension, propylene glycol, polyethylene glycol, vegetable oil such as olive oil, or an injectable ester such as ethyl oleate may be used. As a suppository base, Witepsol, Macrogol, Tween 61, cacao butter, laurin fat or glycerogelatin may be used.

A therapeutically effective amount of the compound including the AzA according to the present disclosure may be measured at an early stage of a cell culture assay. For example, a dose may be calculated in an animal model to obtain a circulation concentration range including a half maximal inhibitory concentration (IC50) or half maximal effective concentration (EC50), determined in cell culture. This information can be used to more exactly determine a useful dose in a human. The dose of the AzA may be changed within the range according to an administration type and an administration route.

The subject into which the AzA of the present disclosure is administered refers to a target into which the AzA or the composition including an effective amount of an AzA or a pharmaceutically acceptable salt thereof as an active ingredient can be administered, and there is no limitation to a target, which includes, for example, a mammal such as a human.

A preferable dose of the AzA or the composition including AzA as an active ingredient according to the present disclosure may vary according to a patient's condition and a body weight, a severity of a disease, a drug type, an administration route and a duration, and may be appropriately selected by one of ordinary skill in the art. However, for a preferable effect, the pharmaceutical composition of the present disclosure may be administered daily at 0.0001 to 1000 mg/kg, preferably 0.5 to 200 mg/kg, and more preferably 0.5 to 100 mg/kg. Administration may be performed one or several times per day. The dose does not limit the range of the present disclosure in any aspect.

The pharmaceutical composition according to the present disclosure may be administered to mammals such as a rat, a mouse, a livestock and a human by various routes such as parenteral administration, oral administration and the like. All administration routes may be expected, and the pharmaceutical composition according to the present disclosure may be administered, for example, orally, or by intrarectal, intravenous, intramuscular, subcutaneous, intrauterine dura mater or intracerebroventricular injection.

In addition, an oral formulation may vary according to a patient's age, sex or body weight, and may be administered at 0.1 to 100 mg/kg one to several times per day. In addition, the dose may be increased/decreased according to an administration route, degree of a disease, sex, body weight, or age. Therefore, the dose does not limit the range of the present disclosure in any aspect.

In the present disclosure, when being provided as a mixture including other components in addition to the AzA, the composition may include the AzA at 0.001 to 99.9 wt %, preferably 0.1 to 99.0 wt %, and more preferably 30 to 50 wt % with respect to the total weight of the composition.

In addition, the present disclosure provides a food composition for preventing, improving, or treating fatty liver, which includes an effective amount of an AzA or a pharmaceutically acceptable salt thereof as an active ingredient. In addition, the AzA may be added to food for improving fatty liver or vascular diseases. When the AzA of the present disclosure is used as a food additive, the AzA may be added alone or in combination with another food or food component, and may be suitably used according to a conventional method. A mixing amount of the active ingredient may be suitably determined according to a purpose of use (prevention, health or therapeutic treatment). Generally, in the manufacture of food or a drink, the AzA of the present disclosure is added at 15 wt % or less, and preferably 10 wt % or less with respect to the raw components. However, in the case of long-term intake for health and hygiene or for health control, the amount may be less than the above range, and since there is no problem in terms of safety, the active ingredient may be used at an amount exceeding the above range.

In the present disclosure, the food includes functional food and health functional food, and the term "functional food" used herein means food improved in functionality compared to a general food by adding the AzA of the present disclosure to the general food. The functionality may be classified into a physical property and physiological function, and when the AzA of the present disclosure is added to the general food, the physical property and physiological function of the general food will be improved, and in the present disclosure, such food with the improved functions is defined overall as "functional food."

The functional food of the present disclosure may be used in various applications such as drugs, foods or beverages for preventing, improving, or treating alcoholic and/or NAFL by reducing the fat accumulation of in liver tissue. There is no particular limitation to a type of food. Examples of food to which the material can be added include meats, sausages, breads, chocolate, candies, snacks, cookies, pizza, ramen, other types of noodles, gums, dairy products including ice creams, various types of soups, beverages, teas, drinks, alcohol drinks and vitamin complexes, and in a common sense, all types of food.

A health drink composition according to the present disclosure may contain various flavoring agents or natural carbohydrates as additional components like a conventional drink. The above-mentioned natural carbohydrates may include monosaccharides such as glucose and fructose, disaccharides such as maltose and sucrose, and polysaccharides such as dextrin and cyclodextrin, and sugar alcohols such as xylitol, sorbitol, erythritol, etc. As sweeteners, natural sweeteners such as thaumatin and a stevia extract, and synthetic sweeteners such as saccharin and aspartame may be used. A proportion of the natural carbohydrates is generally about 0.01 to 20 g, and preferably about 5 to 12 g per 100 mL of the composition of the present disclosure.

In addition to the components, the composition of the present disclosure may contain a variety of nutrients, vitamins, minerals, flavoring agents, coloring agents, pectic acid and a salt thereof, alginic acid and a salt thereof, organic acids, protective colloid thickening agents, pH adjusters, stabilizers, preservatives, glycerin, alcohols, or carbonating agents used in carbonated beverages. In addition, the composition according to the present disclosure may contain flesh for preparing natural fruit juices and vegetable juices. Such ingredients may be used independently or in combination. A ratio of such additive is not particularly limited, but generally selected in a range of 0.01 to 0.20 part by weight with respect to 100 parts by weight of the composition of the present disclosure.

The present disclosure may have various modifications and embodiments, and thus the present disclosure will be described in further detail below. However, the present disclosure is not limited to specific embodiments, and it should be understood that the present disclosure includes all modifications, equivalents and alternatives included in the technical idea and scope of the present disclosure. To explain the present disclosure, if it is determined that a detailed description of the related art may obscure the gist of the present disclosure, the detailed description thereof will be omitted.

Hereinafter, to help in understanding the present disclosure, exemplary examples will be suggested. However, the following examples are merely provided to more easily understand the present disclosure, and not to limit the present disclosure.

EXAMPLES

Example 1. Evaluation of Cytotoxicity of an AzA

An MTT assay was performed to evaluate cytotoxicity of an AzA. The MTT assay is a test method using the ability of mitochondria to reduce a yellow water-soluble substrate, MTT tetrazolium, to a purple water-insoluble MTT formazan, by a dehydrogenase. An MTT reagent was prepared by diluting with phosphate buffered saline (PBS) to a concentration of 2 to 5 mg/mL. Hepa1c1c-7 cells used in the experiment were purchased from the Korean Cell Line Bank, and cultured in a minimum essential medium Eagle alpha modification medium (MEM-alpha, Hyclone) supplemented with 10% FBS and 1% PEST. For the experiment, the Hepa1c1c-7 cells ($4 \times 10^4$ cells/mL) were seeded in a 96-well plate, incubated at 37° C. under 5% $CO_2$ for 24 hours, and cultured for 24 hours with 0 to 500 μM of AzA. After 100 μL of the MTT reagent was added to each sample at 4 mg/mL, the cells were incubated at 37° C. under 5% $CO_2$ for 4 hours, 100 μL of dimethyl sulfoxide (DMSO) was added, and then absorbance was measured at 540 nm. Since the absorbance level is proportional to the number of living cells, a cell death effect caused by toxicity may be quantified by measuring the absorbance level.

The cytotoxicity test for 3T3-L1 adipose cells was performed by a tetrazolium-based colorimetric (MTT) method. The MTT assay is a method for evaluating cytotoxicity by measuring absorbance at a suitable wavelength (usually at 500 to 600 nm) based on a metabolic process, in which a dehydrogenase in mitochondria of intact cells reduces a yellow water-soluble tetrazolium salt [3-(4,5-dimethylthiazol-2-yl)-2-5-diphenyltetrazolium bromide] (MTT) into a water-insoluble dark violet MTT formazan crystal. From the experimental result, as shown in FIG. 1, it was confirmed that, when Hepa1c1c-7 cells and 3T3-L1 adipose cells were treated with 0 to 500 μM of AzA, toxicity was not exhibited at every concentration, compared with the control group.

Example 2. Study of Downstream Signal Transduction Mechanism Through Olfr544 Activation in Response to the AzA Treatment 2-1) Construction of Olfr544 Knockdown Cell Line To more clearly confirm whether an AzA acts as an Olfr544 ligand, an Olfr544 knockdown cell line was constructed using a vector including shRNA, and protein expression levels of normal cells and knockdown cells were compared by performing an experiment as follows. To construct an Olfr544 knockdown cell line, particularly, an oligonucleotide (top strand [SEQ ID NO: 1]: 5'-CACCGCT-CACTGTTCGCATCTTCATTCGAAAATGAAGAT-GCGA-ACAGTGAG-3') encoding an Olfr544-targeted shRNA hairpin sequence or an oligonucleotide (top strand [SEQ ID NO: 2]: 5'-CACCGTAAGGCTATGAAGAGA-TACCGAAGTATCTCTTCATAGCCTTA-3') encoding non-targeting scrambled shRNA hairpins were inserted into an shRNA cloning site of a pENTR/U6 vector using a BLOCK-iT U6 RNAi entry vector kit (Invitrogen). Subsequently, Hepa1c1c-7 or 3T3-L1 cells were seeded on a 6-well plate and transfected with 2.5 μg of Olfr544 shRNA or scrambled shRNA using 10 μL Lipofectamine 2000 (Invitrogen) for 48 hours, thereby constructing an Olfr544 knockdown cell line. The constructed cells were cultured under 5% $CO_2$ at 37° C. under a humidified condition.

2-2) Measurement of cAMP Concentration

A cAMP assay estimates a production level of cAMP, which is a secondary messenger material of a GPCR receptor activated by a ligand, using a cAMP standard calibration curve. A 96 well-plate included in a cAMP Assay ELISA kit (Enzo Life science, New York, USA) was coated with a GxR IgG antibody, and cAMP in a blue solution for plotting the standard calibration curve, binds with alkaline phosphatase and turns into yellow color by the rabbit antibody. When pNpp substrate is added into the wells bound with cAMP, alkaline phosphatase is activated to cause the color changes, and a cAMP concentration may be measured through colorimetric quantification at a wavelength of 405 nm.

In this experiment, Hepa1c1c-7 cells were seeded on a 96-well plate at $1 \times 10^4$ cells/well for differentiation, and treated with 50 μM of AzA and 1 μM of Forskolin (FSK), which is a positive control, for 18 hours, and then a cAMP concentration was measured according to the above-described method.

2-3) Protein Extraction

Hepa1c1c-7 cells (or adipose tissue) were rinsed with phosphate-buffered saline (PBS), and then a cell (or tissue) pellet was only collected. The pellet was washed with solution C (120 mM NaCl, 5 mM KCl, 1.6 mM $MgSO_4$, 25 mM $NaHCO_3$, 7.5 mM D-glucose, pH 7.4), treated with solution D (solution C+10 mM $CaCl_2$), and stirred for 20 minutes to perform centrifugation. After the centrifugation, the obtained supernatant was centrifuged again, a precipitate obtained thereby was suspended in a TEM buffer (10 mM Tris, 3 mM $MgCl_2$, 2 mM EDTA, pH 8.0) and glycerol and thus finally obtained as membrane protein fractions. The above-described protein extraction method is known as calcium ion bombardment, which exhibits a higher protein yield than a mechanical stirring method, which is a conventional cell membrane fractionation method. Meanwhile, in the case of a cytosol protein fraction, Hepa1c1c-7 cells (or adipose tissue) were rinsed with PBS, only a pellet was collected, the pellet was treated with a digitonin-containing buffer (150 mM NaCl, 50 mM HEPES, 25 μg/mL digitonin, pH 7.4), and the resulting solution was maintained on ice for 10 minutes and then centrifuged, thereby finally obtaining a supernatant as a cytosol protein fraction. Meanwhile, when a whole protein extract was obtained without fractionation, Hepa1c1c-7 cells were treated with a cell lysis buffer (50 mM Tris, 1% Triton-X 100, 1 mM EDTA, proteinase inhibitor (PI)) to lyse the cells, and centrifuged at 13,000 rpm and 4° C. for 20 minutes, thereby obtaining a supernatant.

2-4) Protein Electrophoresis (SDS-PAGE) and Western Blotting

To confirm whether an Olfr544 protein was expressed, protein fractions (cell membrane protein, cytosol protein) and total proteins (whole protein extract), which were extracted by the method of Example 2-3, were quantified by a Bradford method. Each sample was subjected to 12% SDS-PAGE using about 40 μg of the protein, which was modified by suitably heating and/or lysing according to the type of an extracted protein (fractionated protein, total proteins or phosphorylated protein). Western blotting was performed by blocking to prevent non-specific binding to a nitrocellulose membrane (NC membrane) containing a protein blotted from a SDS-PAGE gel, sequentially treating a primary antibody (an anti-Olfr544 rabbit antibody (Abcam, UK) and an anti-β-actin antibody (loading control, Santa Cruz, Calif., USA)) and a secondary antibody (HRP-conjugated-anti-rabbit IgG, Santa Cruz, Calif., USA) against a protein to be detected, and then treating each at room temperature for 1 hour. The expression level of each gene was standardized using β-actin or GAPDH expression, and the comparison of the contents of protein bands of western blots was quantified and digitized using software (Gel-Pro Analyzer 4.0). All antibodies used in western blotting were purchased from Santa Cruz Biotechnology (Santa Cruz, Calif. USA).

Figure 2A:
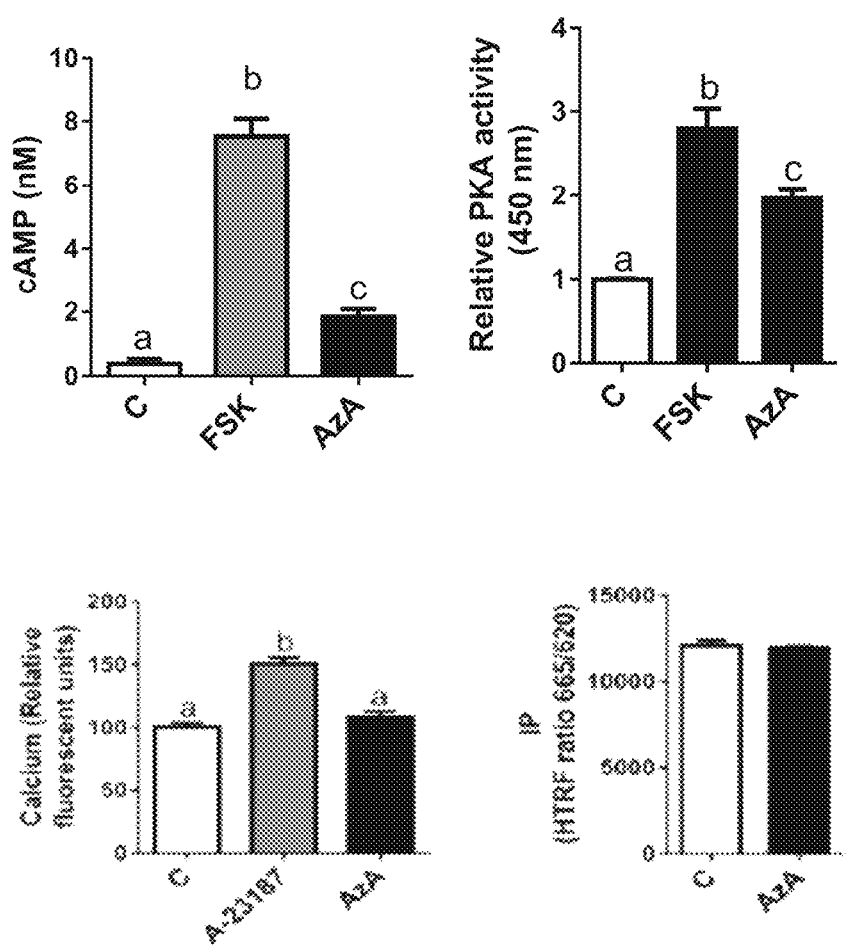
FIGS. 2A to 2C show cAMP-PKA-CREB mechanism activity in response to the AzA treatment in Hepa1c1c-7 cells. Specifically.

2-5) Olfr544 Activation by an AzA and Confirmation of Downstream Signal Transduction Pathway Thereof As shown in FIG. 2A, it was confirmed that, when Hepa1c1c-7 cells were treated with an AzA, cAMP and calcium concentrations in the cells are significantly increased, compared with the control group, and PKA activity is also significantly increased by the AzA treatment.

Figure 2B:
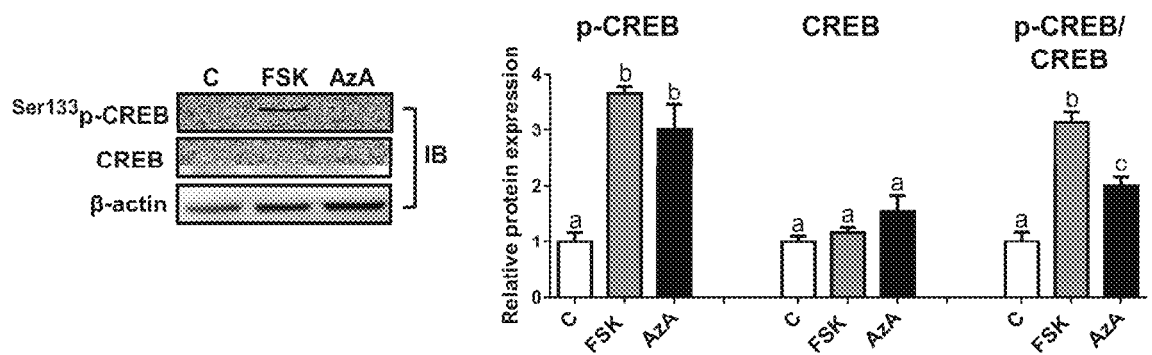

In addition, as shown in FIG. 2B, it can be confirmed that CREB activity was increased by phosphorylation in the AzA-treated group, and thus a p-CREB/CREB ratio was significantly increased.

Figure 2C:
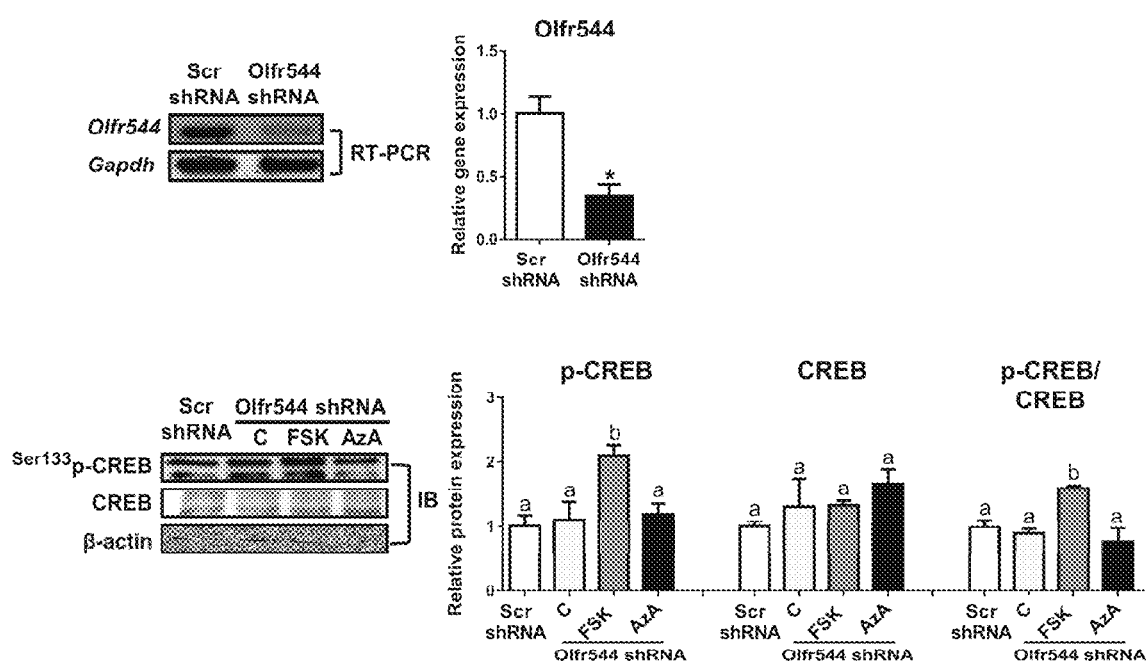

On the other hand, as can be seen in FIG. 2C, in cells in which Olfr544 knockdown was performed by transfection, an increase in a p-CREB/CREB ratio was not observed.

Taken together, it can be seen that an AzA acts as an Olfr544 ligand to activate a cAMP-PKA-CREB signal transduction mechanism.

Example 3. Confirmation of the Effect of an AzA on PPARα Activity 3-1) Quantitative Real-Time PCR (qPCR)

To confirm the change in PPARα gene expression level by an AzA, Hepa1c1c-7 cells were seeded onto a 24-well plate at $5\times10^5$ cells/mL, cultured for 24 hours, and treated with 50 μM of AzA for 2 hours. Subsequently, RNA was extracted, and cDNA synthesis was performed from the extracted RNA using a ReverTra Ace® qPCR RT kit (TOYOBO, Osaka, Japan). More specifically, to increase PCR efficiency, the extracted RNA was treated at 65° C. for 5 minutes, and the resulting product was immediately stored on ice. Subsequently, a total of 8 μL of a reaction mixture was prepared with 2 μL of a 4×DNA Master Mix containing a gDNA remover, 0.5 μg of RNA and distilled water (nuclease-free water), and reacted at 37° C. for 5 minutes. Subsequently, a 5×RT Master mix was added to the reaction mixture, reacted at 37° C. for 5 minutes, at 50° C. for 5 minutes and at 98° C. for 5 minutes to synthesize cDNA. The cDNA synthesized by the above method was subjected to qPCR using a THUNDERBIRD SYBR qPCR Mix (TOYOBO) and an iQ5 iCycler system (Bio-Rad, California, USA) according to a method known to those of ordinary skill in the art. More particularly, amplification was performed with initial denaturation at 95° C. for 4.5 minutes, and 40 cycles of additional denaturation at the same temperature for 10 seconds, annealing and cooling at 55 to 60° C. for 30 seconds, and elongation at 68° C. for 20 seconds. The degree of expression of each gene was standardized using GAPDH expression. Primers were designed using the Nucleotide BLAST software of the National Center for Biotechnology Information (NCBI), and purchased from Bionics (Seoul, Korea).

3-2) Measurement of Fatty Acid Oxidation Rate

Hepa1c1c-7 cells were seeded on a 24-well plate at $5\times10^5$ cells/mL, cultured for 24 hours, treated with 100 μM of AzA, and then incubated for 24 hours. Afterward, [1-$^{14}$C]palmitate was accumulated, the cells were cultured for one hour, and the medium was collected to extract $CO_2$ using NaOH and HCl, followed by measuring $^{14}CO_2$ using a liquid scintillation counter. As a positive control, GW7647 (1 μM) was used.

3-3) PPRE-Luciferase Assay

To measure PPRE-luciferase, HEK293 cells (Korean Cell Line Bank) seeded on a 24-well plate at $2\times10$ cells/well were used. pSG5-PPAR alpha (Addgene, MA, USA) was co-transfected according to a given protocol using pCMV-3× PPRE-Luc, a Renilla expression vector and Lipofectamine 2000 (Invitrogen). After 24-hour post-transfection, the cells were treated with various concentrations of an AzA, and then analyzed using a dual luciferase assay kit (Promega, Fitchburg, Wis., USA) and Victor X2 (PerkinElmer, Santa Clara, Calif.). A luciferase fluorescent signal was standardized using Renilla.

3-4) PPARα Activation by an AzA and Mechanism Thereof

Figure 3:
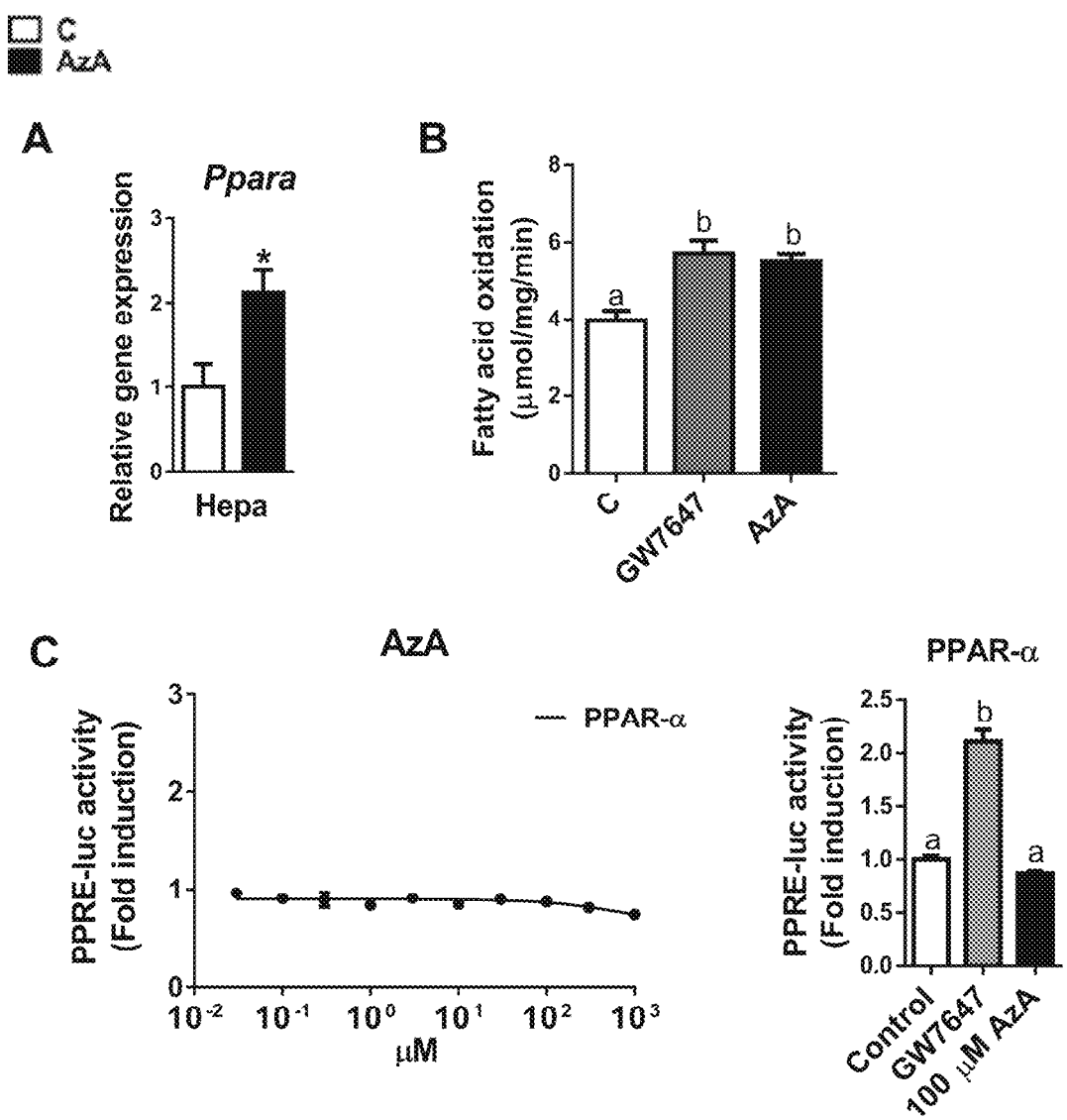
FIG. 3 shows (A) the increase in PPARα gene expression in response to the AzA treatment in Hepa1c1c-7 cells, (B) the increase in fatty acid oxidation rate, and (C) the increase in PPARα activity, confirmed by PPRE-luciferase assay.

As shown in FIG. 3, AzA treatment induced a significant increase in PPARα expression in Hepa1c1c-7 cells (A) and a fatty acid oxidation rate was significantly increased (B), compared with the control group. By using PPRE-luciferase, when fat oxidation increases through PPARα activation by an AzA, it was confirmed that an AzA does not act as a direct ligand for PPARα (C). According to the above result, it was confirmed that an AzA activates Olfr544, and then cAMP-PKA-CREB is activated, which in turn increases a fatty acid oxidation rate.

Example 4. Confirmation of Fatty Liver Inhibitory Effect of an AzA in Fatty Liver-Induced Mouse 4-1) Construction of the Experimental Animal Model Mice used in the example, which were an eight-week-old C57BL/6J model, were purchased from Samtako, and Olfr544 KO mice were manufactured by Macrogen based on the C57BL/6J model using a CRISPR/Cas9 system. All experiments performed in the example are compliant to a protocol approved by the Animal Experiment Ethics Committee at Korea University (Protocol No. KUIACUC-20170322-1). The mice were acclimated at 21 to 25° C. under a 50 to 60% relative humidity condition for 12 hours before being used in the experiments, and a total of 18 mice were treated with an AzA diluted with distilled water at 50 mg/kg of body weight and distilled water as a control through oral administration for 6 weeks. The mice used in the experiments were fed a high-fat diet containing 60% fat (D12492, Research Diets, Inc) to induce fatty liver, and then a body weight was measured every week.

4-2) Analysis of Triglyceride Concentration in Liver Tissue

The measurement of the concentration of triglycerides in liver tissue was performed by homogenizing the obtained liver tissue of a mouse in 600 μL of acetone (Daejung, Korea), storing the homogenate at 4° C. for 24 hours, and obtaining a fat part by centrifugation at 12000 rpm for 10 minutes. The fat part was dried, dissolved in 95% ethanol, quantified using a Cobas C11 autoanalyzer (Roche, Basel, Switzerland), and normalized with a liver weight.

4-3) Analyses of PPARα and Downstream Gene Expression in Liver Tissue

RNA was extracted from liver tissue, and the expression of PPARα and PPARα downstream genes such as Acox1, Cpt1a and Hmgcs2 were analyzed by qPCR according to the method of Example 3-1 described above.

4-4) Measurement of Fatty Acid Oxidation Rate

To evaluate fatty acid oxidation, 100 mg of liver tissue was homogenized in a 0.25 M cold sucrose solution, centrifuged at 600 rpm and 4° C. thereby obtaining a supernatant, and then 50 μL of 10% Triton X-100 was added to 450 μL of the supernatant. Subsequently, 5 μL of the sample was mixed with 950 μL of 50 mM Tris-HCl, 10 μL of 20 mM NAD, 3 μL of 0.33 M dithiothreitol, 5 μL of 1.5% BSA, 5 μL of 2% Triton X-100, 10 μL of 10 mM CoA, and 10 μL of 1 mM FAD. The mixture was mixed with 2 μL of 5 mM palmitoyl-CoA, reacted at 37° C. and analyzed at 340 nm for 5 minutes using a spectrophotometer.

4-5) Indirect Calorimetric Assay

A C57BL/6J mouse and an Olfr544 KO mouse were treated with HFD and an AzA for 6 weeks and housed in a metabolic cage for three days, and the result at day 3 was analyzed as an experimental result. An oxygen consumption amount ($VO_2$) and a carbon dioxide production amount (VCO$_2$) were analyzed using an Oxylet Physiocage System (Panlab/Harvard apparatus, Cornella, Spain) and suiteMETABOLISM (V2.2.01, Panlab) software. A respiratory quotient (RQ) was calculated using the formula VCO$_2$/VO$_2$, and energy expenditure was analyzed using the formula EE=VO$_2$×1.11×(3.815+1.232×RQ). The oxidation of a free fatty acid was calculated using the formula (1.6946×VO2)−(1.7012×VCO$_2$).

Figure 4A:
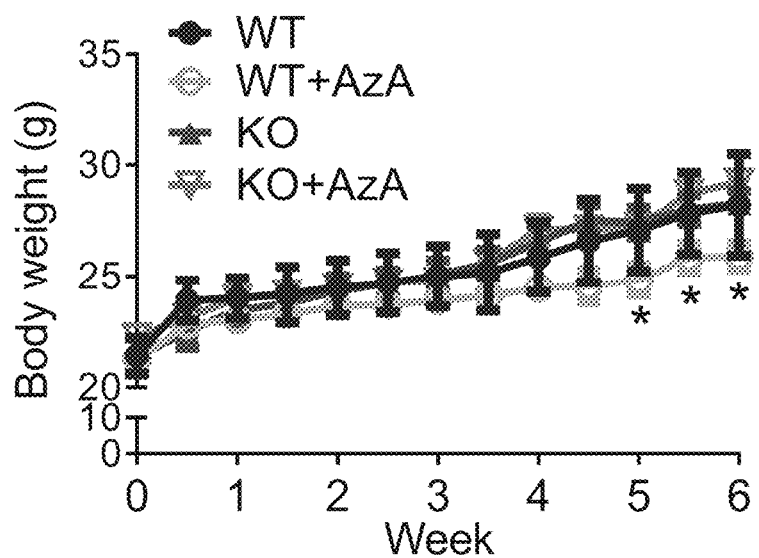
FIGS. 4A to 4E show a fatty liver inhibitory effect in response to the AzA treatment in a fatty liver-induced mouse. Specifically.
Figure 4B:
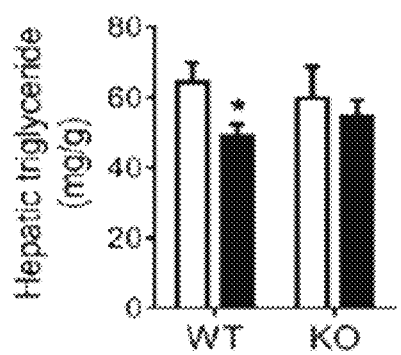
Figure 4C:
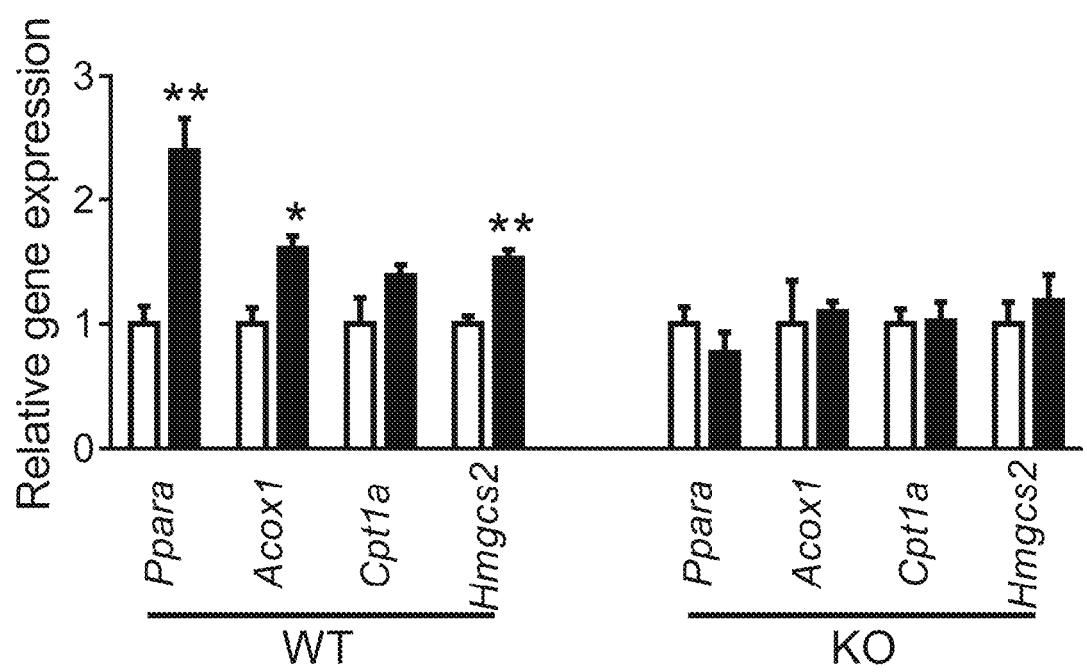
Figure 4D:
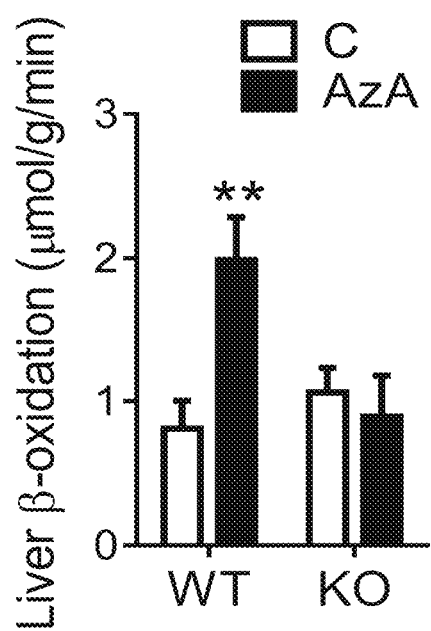
Figure 4E:
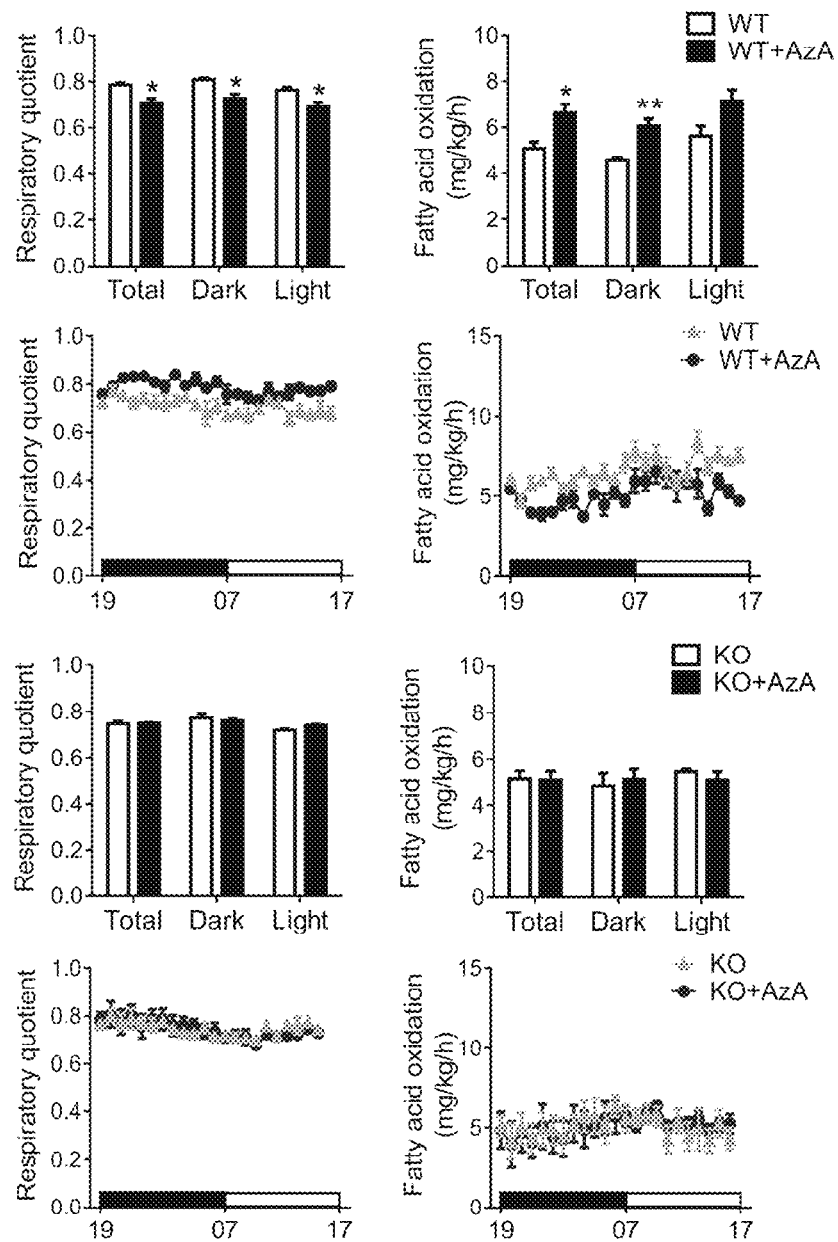

4-6) Confirmation of Fatty Liver Inhibitory Effect of an AzA in Fatty Liver-Induced Mouse Through the experiment, it was confirmed that body weight was decreased compared with the control group, when an AzA was orally administered for 6 weeks as well as a high-fat diet (FIG. 4A), and a triglyceride concentration in liver tissue was also decreased (FIG. 4B). In addition, expression of PPARα and a target gene thereof in liver tissue was significantly increased (FIG. 4C), and then it was confirmed that a fatty acid oxidation rate was increased, compared with the control group, by measuring a fatty acid oxidation rate in liver tissue (FIG. 4D). As a result of the indirect calorimetric analysis, a decrease in the respiratory quotient and an increase in the oxidation of free fatty acids were confirmed, confirming that fatty acid oxidation in a mouse was stimulated by the AzA. However, these effects were not shown in an Olfr544 KO mouse, in which Olfr544 was knocked down (FIG. 4E). These results show that long-term administration of an AzA can reduce the body weight of a subject and reduce a triglyceride concentration in liver tissue, and the AzA increases the expression of PPARα and a target gene thereof in liver tissue and stimulates fatty acid oxidation. According to these results, it can be shown that the long-term administration of an AzA reduces fatty liver, and this effect is exhibited in an Olfr544-dependent manner.

Figure 4F:
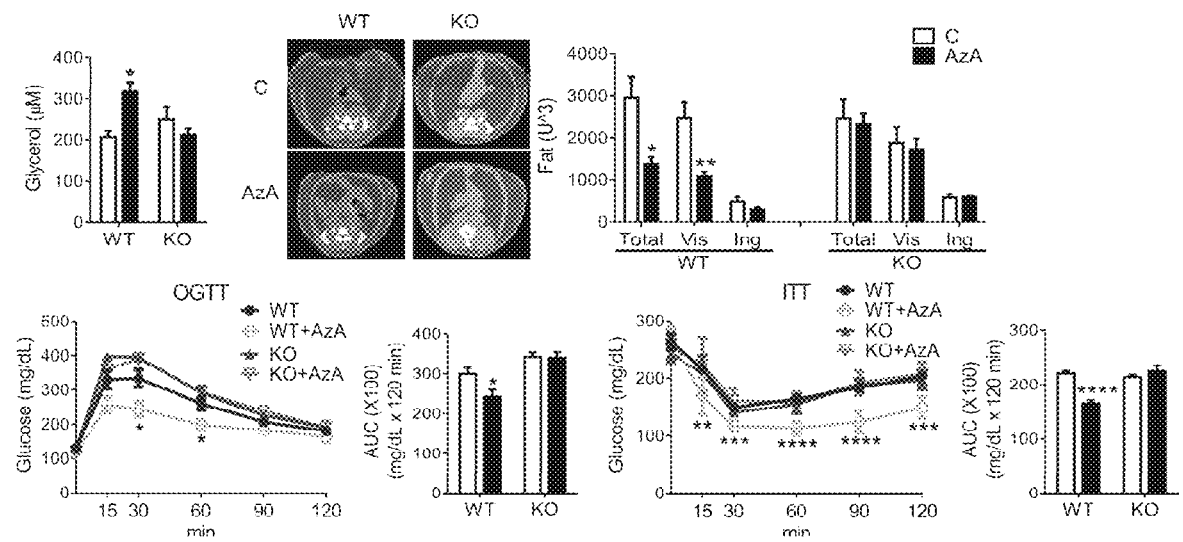
FIG. 4F shows the comparison of a blood glycerol concentration, a body fat level and an insulin sensitivity after the AzA is administered into HFD, WT and KO mice for a long time.

4-7) Comparison of Blood Glycerol Concentration, Body Fat Amount, and Insulin Sensitivity after Long-Term Administration of an AzA in HFD, WT and KO Mice An AzA (100 mg/kg) was intraperitoneally administered, and then concentration of a glycerol, which is a body fat decomposition marker, was measured. As a result, the AzA stimulated the decomposition of body fats in a WT mouse, but there was no effect in a KO mouse. When an AzA was administered to WT and KO mice at 50 mg/kg/day and a body fat amount was analyzed through a microCT method, a total fat amount and abdominal fat were significantly decreased in a WT mouse, but there were no such effects in a KO mouse, confirming that an AzA stimulates body fat decomposition through Olfr544 activation (FIG. 4F). To measure glucose resistance and insulin resistance, a glucose and insulin resistance test was performed under a condition, in which glucose (1.5 kg/bw) and insulin (0.35 unit/kg/bw) are administered to a mouse. As a result, it was shown that an AzA significantly improved glucose and insulin resistance in a WT mouse, but such an effect was not observed in a KO mouse, confirming that the AzA improved glucose resistance and insulin resistance.

Example 5. Confirmation of Fatty Liver Inhibitory Effect of an AzA in Ob/Ob Mouse 5-1) Experimental Animal Model A 7-week-old male fatty liver model ob/ob mouse was purchased from Central Laboratory Animal Inc. to be used in an experiment. An AzA was orally administered at 50 mg/kg of body weight along with a 60% high-fat diet (HFD) for 6 weeks. As the experiment progresses, body weight was measured once a week, and food intake was measured three times twice a week on the last week.

5-2) Analysis of Triglyceride Concentration in Liver Tissue

The concentration of triglycerides in liver tissue was measured by homogenizing liver tissue of a mouse in 600 μL of acetone (Daejung, Korea), storing the homogenate at 4° C. for 24 hours, and obtaining a fat part by centrifugation at 12000 rpm for 10 minutes. The fat part was dried, dissolved in 95% ethanol, quantified using a Cobas C11 autoanalyzer (Roche, Basel, Switzerland) and normalized with a liver weight.

5-3) Measurement of Fatty Acid Oxidation Rate

A fatty acid oxidation rate was measured and analyzed by the method of Example 4-4 described above.

5-4) Confirmation of Fatty Liver Inhibitory Effect of an AzA in Ob/Ob Mouse

Figure 5A:
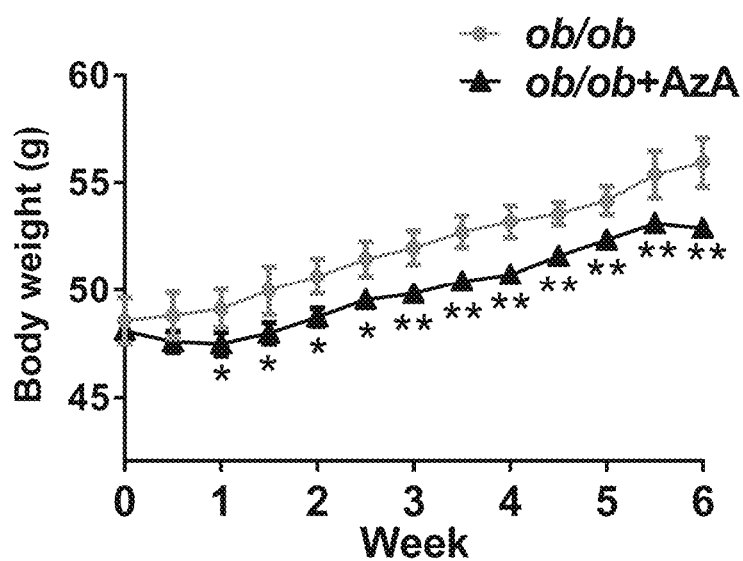
FIGS. 5A to 5C show a fatty liver inhibitory effect in response to the AzA treatment in ob/ob mice. Specifically.
Figure 5B:
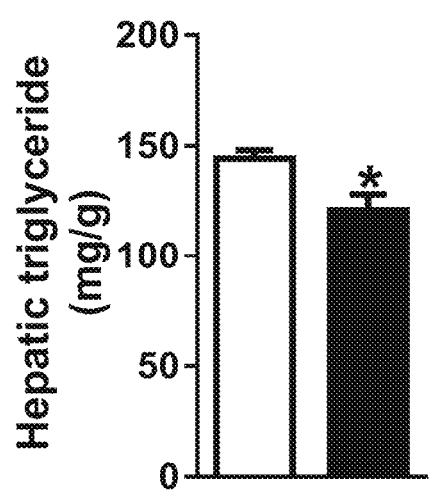
Figure 5C:
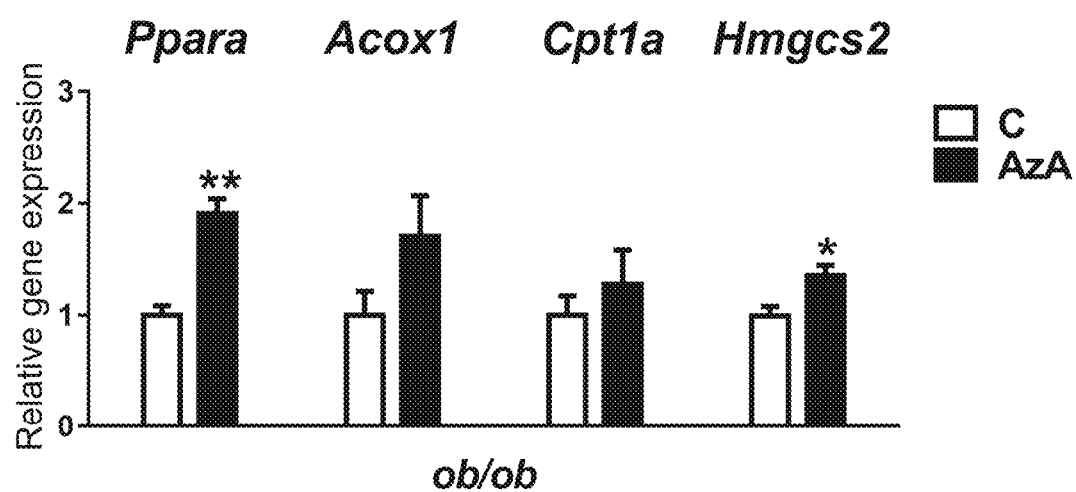

Through the experiment above, it was confirmed that body weight was decreased compared with the control group when an ob/ob mouse was orally administered an AzA for 6 weeks along with a high-fat diet (FIG. 5A), and that a triglyceride concentration was reduced in liver tissue (FIG. 5B). In addition, it was confirmed that the expression of PPARα and a target gene thereof is significantly increased in liver tissue (FIG. 5C). These results show that the long-term administration of an AzA reduced body weight of the ob/ob mouse, a triglyceride concentration was reduced in liver tissue, and the gene expression of PPARα and a target gene thereof, Hmgcs2, was significantly increased in liver tissue. According to these results, it can be seen that an AzA can oxidize fats accumulated in the liver, thereby exhibiting a fatty liver preventing, improving, and treating effect, and thus can be used in various forms.

Figure 5D:
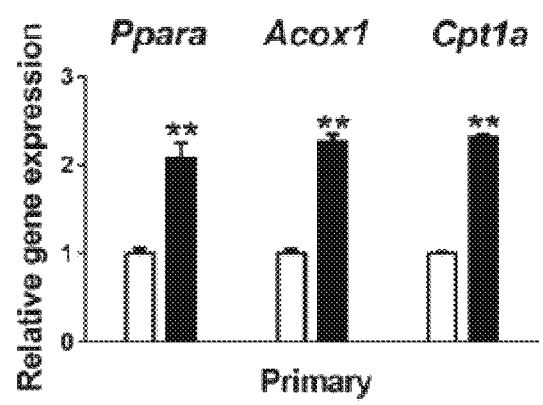
FIG. 5D shows the effect of lipolysis by the AzA in liver tissue of mouse primary hepatocytes.

5-5) Confirmation of Liver Tissue Lipolytic Effect of an AzA in Mouse Primary Hepatocyte To reconfirm the liver tissue lipolytic effect of an AzA, an additional experiment was performed using a mouse primary hepatocyte. From the result of the experiment, it was confirmed that an AzA significantly increases key gene markers such as Ppara, Acox1 and Cpt1a, which are involved in the decomposition of fatty acids, even in mouse primary hepatocytes just like in a liver tissue cell line, that is, Hepa1c1c cells (FIG. 5D). Therefore, it was reconfirmed that an AzA stimulates fatty acid oxidation, thereby treating/preventing a fatty liver lesion.

Figure 6:
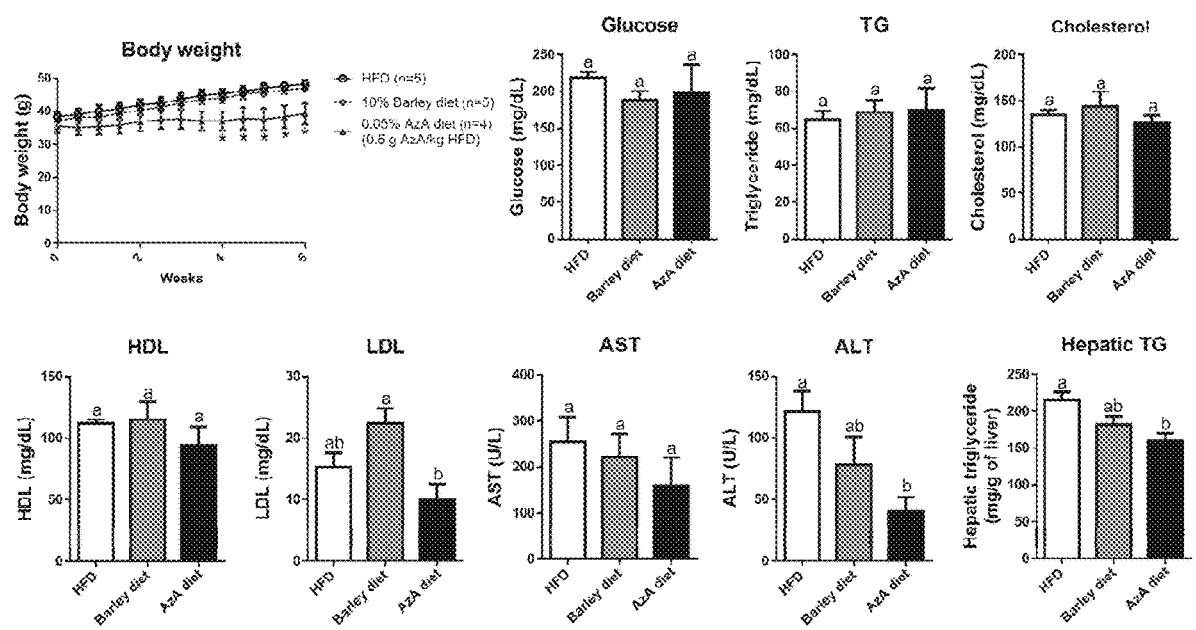
FIG. 6 shows the comparison of a body weight, a blood glucose, a blood glycerol concentration, and a cholesterol concentration between mice fed an HFD along with an AzA diet and mice fed a barley-added diet.

Example 6. Comparison of Body Weight, Blood Glucose, Blood Glycerol Concentration and Cholesterol Concentration in Mice after HFD, AzA- and Barley-Added Diets To reconfirm the fatty liver treatment inhibitory effect of an AzA, an experiment was carried out in comparison with a barley-added diet, which has been known to have a fatty liver preventing effect. A diet, in which an AzA (0.5 g/kg diet) or 10% (w/w) barley was added to a high-fat diet, was administered to mice for 6 weeks. As a result, there was no difference in body weight between a high-fat diet group and barley-added diet group, whereas the body weight was significantly decreased in the AzA group. While there were no differences in fasting blood glucose, triglyceride, total cholesterol and HDL cholesterol concentrations between groups, an LDL cholesterol concentration was significantly decreased in the AzA group. In the case of hepatotoxicity markers such as AST and ALT, an ALT concentration was decreased, and thus liver tissue damage was protected in the AzA group. In addition, when the concentration of a fatty liver lesion marker, i.e., a triglyceride, in liver tissue was measured, it was shown that the concentration was significantly decreased in the AzA group, and thus an excellent effect of alleviating fatty liver was exhibited compared with a barley-added diet, which is generally known as having an effect of alleviating fatty liver (FIG. 6).

Example 7. Effect of Reducing Inflammation by an AzA in Hepa1c1c-7 Cells 7-1) Cell Culture Mouse hepatocytes, i.e., Hepa1c1c-7 cells were purchased from the Korean Cell Line Bank (Seoul, Korea). The Hepa1c1c-7 cells were cultured in a minimum essential medium Eagle alpha modification medium (MEM-α, Hyclone) supplemented with 10% FBS and 1% PEST under conditions of 5% $CO_2$ and 37° C.

7-2) Induction of Inflammation by LPS and Treatment of an AzA

Mouse hepatocytes, i.e., Hepa1c1c-7 cells were seeded on a 96 well-plate at $1\times10^4$ cells/well and cultured for 24 hours, and transfected with a construct including a transcription factor promoter and a luciferase for 8 hours. The experiment was performed on two groups, i.e., a group with inflammation in hepatocytes caused by LPS and a group not being treated with LPS. In the non-treated control, 50 μM of AzA was treated for 6 hours, and in the experimental group, inflammation was induced by treating 100 ng/mL of LPS, the inflammation-inducing material, for 1 hour, and then 50 μM of AzA was treated for 6 hours. As a result, downstream pathway, which was activated by an AzA, was confirmed.

7-3) Experiment for 10 Signal Transduction Pathways of GPCR

To confirm a mechanism of an anti-inflammatory effect of an AzA, 10 transcription factors for signal transduction of GPCR were analyzed. The prior art showed that an AzA activates olfactory receptor Olfr544, which is GPCR in 3T3L1 cells, mouse pre-adipose cells, and the mechanism of Olfr544 promotes lipolysis through a cAMP-CREB signal transduction process (Korean Patent No. 10-15932539). Based on the Olfr544-cAMP-CREB signal transduction process of an AzA, the change of a complicated downstream signal transduction pathway system in response to GPCR activation and inhibition was examined using 10 types of transcription factors through a GPCR 10-pathway reporter assay.

A GPCR 10-signal transduction pathway measurement is a method for assessing a representative signal pathway of GPCR using a reporter gene assay method, and the change of a complicated downstream signal transduction pathway system in response to the activation and inhibition of GPCR can be assessed using 10 types of transcription factors. A GPCR Signaling 10-pathway Reporter Array (QIAGEN, Netherlands) used in this example includes a transcription factor inducing downstream signal transduction and a firefly luciferase construct in each experimental group, and is based on a principle, in which luciferase activity is measured by continuously expressing a Renilla luciferase construct. The 10 types of transcription factors are as follows: ATF2/ATF3/ATF4, CREB, ELK1/SRF, FOS/JUN, MEF2, GLI, FOXO, STAT3, NFAT, and NFκB. In this example, the luciferase activity was measured using a dual luciferase assay kit (Promega, USA) and Victor™ X2 (PerkinElmer, CA, USA).

7-4) cDNA Synthesis

1 μg of RNA extracted from Hepa1c1c-7 hepatocytes was used to synthesize cDNA by using a ReverTra Ace® qPCR RT kit (TOYOBO, Osaka, Japan). More particularly, to increase the efficiency of an RT-PCR reaction, the extracted RNA was treated at 65° C. for 5 minutes, and immediately stored on ice. Afterward, a total of 8 μL of a reaction mixture was prepared with 2 μL of a 4×DNA Master Mix containing a gDNA remover, 0.5 μg of RNA and distilled water (nuclease-free water), and reacted at 37° C. for 5 minutes. And then, a 5×RT Master mix was added to the reaction mixture, reacted at 37° C.-5 min, 50° C.-5 min and 98° C.-5 min to synthesize cDNA.

7-5) Quantitative Real-Time PCR (qPCR)

PCR was performed with the cDNA synthesized by the above-described method using a THUNDERBIRD SYBR qPCR Mix (TOYOBO, Osaka, Japan) and an iQ5 iCycler system (Bio-Rad, California, USA). More particularly, amplification was performed with initial denaturation at 95° C. for 4.5 minutes, and 40 cycles of additional denaturation at the same temperature for 10 seconds, annealing and cooling at 55 to 60° C. for 30 seconds, and elongation at 68° C. for 20 seconds. The expression level of each gene was normalized using GAPDH expression. Primers were designed using the Nucleotide BLAST Software of the National Center for Biotechnology Information (NCBI), and purchased from Bionics (Seoul, Korea).

7-6) Analyses of IL-6 and TNF-α Cytokine Concentrations in Hepa1c1c-7 Cells

Hepa1c1c-7 cells were cultured in a 12-well plate for 24 hours. Subsequently, the cells were pretreated with 50 μM of AzA for 1 hour, and treated with 100 ng/mL LPS for 6 hours with the AzA present. The Hepa1c1c-7 cells were lysed in a cell lysis buffer (50 mM Tris, 1% Triton-X 100, 1 mM EDTA, proteinase inhibitor), centrifuged at 13,000 rpm and 4° C. for 20 minutes, thereby obtaining a supernatant, and then the supernatant was analyzed using a Mouse IL6 ELISA kit and a Mouse TNFα ELISA kit (Thermo Scientific, IL, USA). Tumor necrosis factor-alpha (TNF-α) and interleukin-6 (IL-6) were quantified using ELISA known to those of ordinary skill in the art.

Figure 7A:
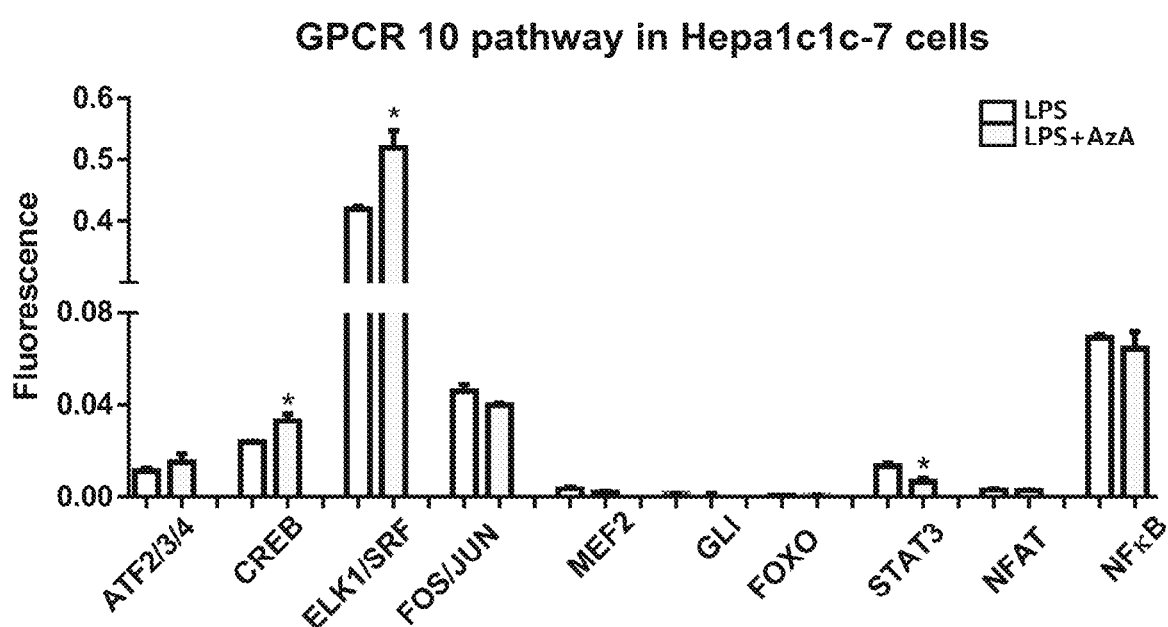
FIGS. 7A to 7C show that an inflammatory response is inhibited when Hepa1c1c-7 cells in which inflammation is induced by LPS are treated with the AzA. Specifically.

7-7) Confirmation of the Effect of Reducing Inflammation by an AzA in Hepa1c1c-7 Cells According to the method described in Example 7-3, a result of analyzing that transcription factors of an inflammation-associated GPCR-dependent signal transduction pathway are changed by an AzA in mouse hepatocytes, i.e., Hepa1c1c-7 cells, is shown in FIG. 7A. As can be seen in FIG. 7A, after the inflammation was induced by treating Hepa1c-7 cells with LPS, the transcription factors having significant activities for the AzA effect were CREB, ELK1/SRF and STAT3, which are associated with cAMP/PKA, MAPK/ERK, IL-6 signaling pathways, respectively.

Figure 7B:
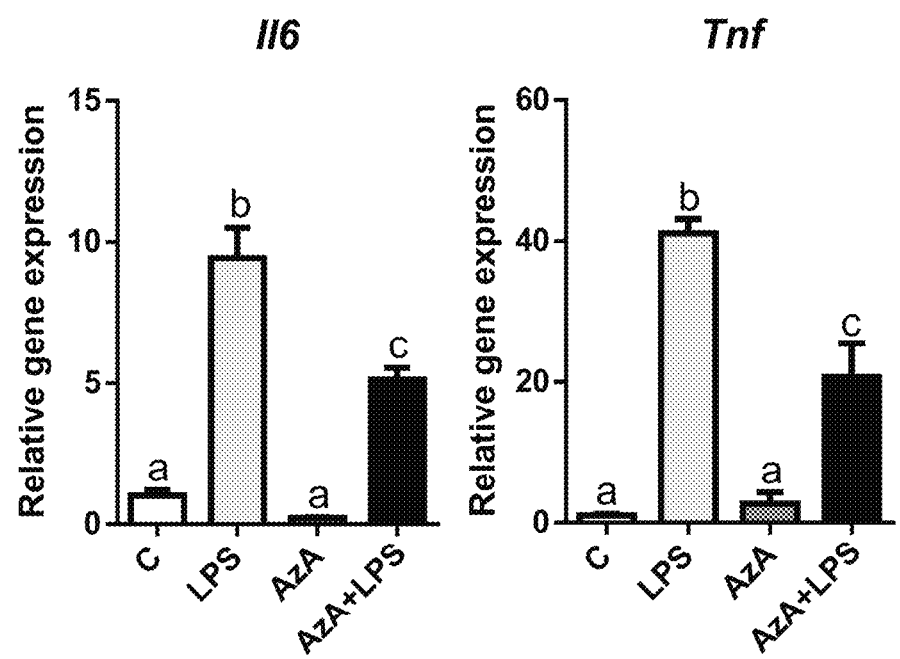

In addition, the results of measuring the gene expression of inflammatory response-mediated materials IL-6 and TNF-α in mouse hepatocytes, Hepa1c1c-7 cells, through qPCR according to the methods described in Example 7-4 and 7-5 were quantified, and shown by a graph in FIG. 7B. As shown in FIG. 7B, when a control group was treated with LPS, it was confirmed that IL-6 and TNF-α gene expression was increased. In contrast, in the AzA-treated group, it was confirmed that IL-6 and TNF-α gene expression was significantly decreased, compared with the control group.

Figure 7C:
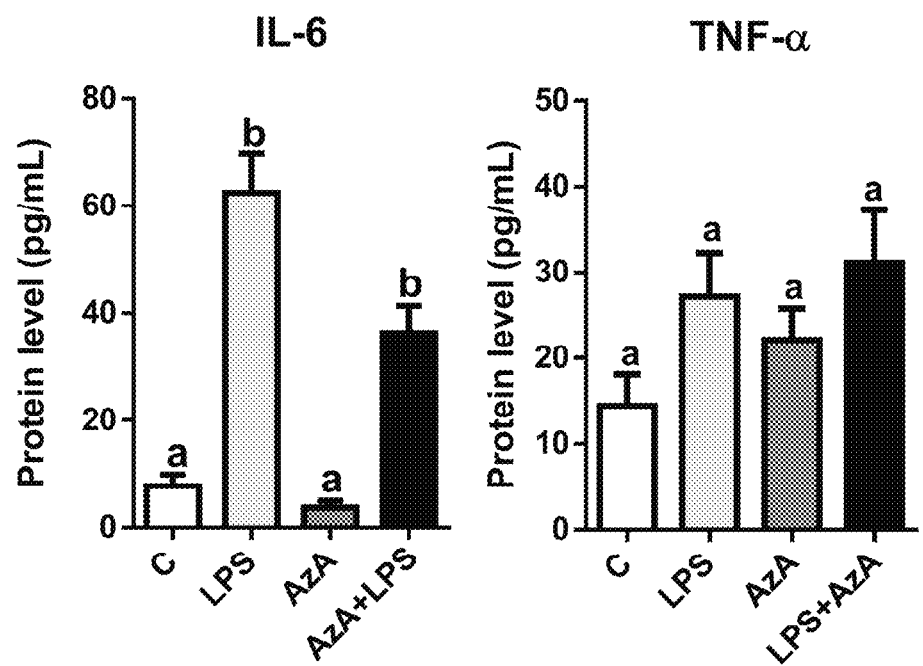

In addition, inflammatory response-mediated materials, i.e., inflammatory cytokines such as IL-6, TNFα and IL-1l3, were analyzed in Hepa1c1c-7 hepatocytes according to the method of Example 7-5, and the result is shown in FIG. 7C. As can be seen in FIG. 7C, by the treatment with the AzA, there was a tendency of decrease in the expression level of the IL-6 protein.

This result means that Olfr544 activity stimulates ELK1/SRF, STAT3 and CREB activities in LPS-induced Hepa1c1c-7 cells, an AzA reduces the expression of Il6 and Tnf genes in Hepa1c1c-7 cells, and reduces the concentration of the IL-6 cytokine. Therefore, the potential anti-inflammatory function of an AzA was confirmed through Olfr544 activation in the cultured liver cells.

Example 8. Effect of Reducing Inflammation by an AzA in 3T3-L1 Cells 8-1) Cell Culture 3T3-L1 cells, mouse pre-adipose cells were purchased from the Korean Cell Line Bank (Seoul, Korea). The 3T3-L1 cells were cultured in Dulbecco's modified Eagle's medium (DMEM) supplemented with 10% heat-inactivated bovine calf serum (Gibco, Grand Island, N.Y., USA) and 1% PEST under 5% $CO_2$ at 37° C. The 3T3-L1 pre-adipose cells were seeded on a 6-well plate at $1\times10^6$ cells/well to differentiate into adipose cells, and cultured to a density of 100%. After 2 days, the cultured 3T3-L1 pre-adipose cells were incubated in DMEM containing 10% fetal bovine serum (FBS) and an MDI solution (0.5 mM IBMX, 0.5 μM dexamethasone and 10 μg/mL insulin) for 3 days. Subsequently, the treated cells were cultured in DMEM containing 10% FBS and 10 μg/mL insulin, and the formation of lipid droplets in cells and the degree thereof were confirmed, and based on this, the differentiation into adipose cells was confirmed.

8-2) Induction of Inflammation by LPS and an AzA Treatment

3T3-L1 adipose cells were seeded on a 96 well-plate at $1\times10^4$ cells/well and cultured for 24 hours, and transfected with a construct including a transcription factor promoter and a luciferase for 8 hours. An experiment was carried out on two groups, i.e., a group with inflammation in hepatocytes caused by LPS and a group without being treated with LPS. The non-treated control was treated with 50 μM of AzA for 6 hours, and the experimental group was treated with 100 ng/mL of the inflammation-inducing material LPS for 1 hour to induce inflammation. As a result, a downstream pathway activated by an AzA was confirmed in cells treated with 50 μM of AzA for 6 hours.

8-3) Experiment for 10 Signal Transduction Pathways of GPCR

To confirm a mechanism of an anti-inflammatory effect of an AzA, 10 transcription factors for signal transduction of GPCR were analyzed by the same method as described in Example 7-3.

8-4) Confirmation of Expression of IL-6 and TNF-α Genes

To confirm the expression of IL-6 and TNF-α genes, qRT-PCR was performed by the same methods described in Examples 7-4 and 7-5.

8-5) Confirmation of Inflammation Reducing Effect of an AzA in 3T3-L1 Cells

Figure 8A:
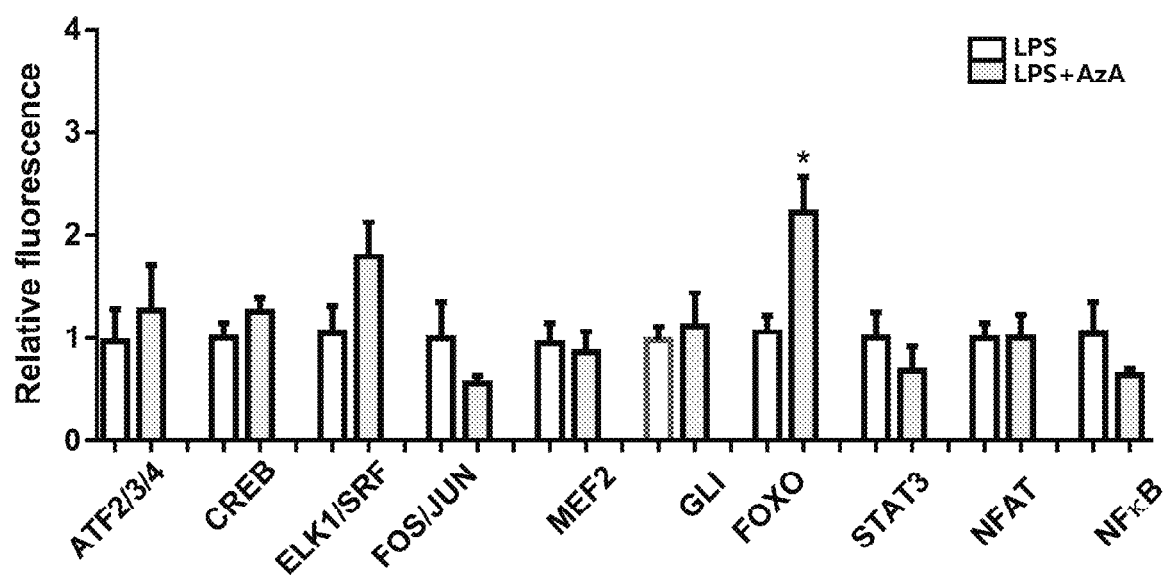
FIGS. 8A and 8B show that an inflammatory response is inhibited when 3T3-L1 cells in which inflammation is induced by LPS are treated with the AzA. Specifically.

According to the method described in Example 8-3, a result of analyzing that transcription factors of an inflammation-associated GPCR-dependent signal transduction pathway are changed by an AzA in mouse adipose cells, i.e., 3T3-L1 cells, is shown in FIG. 8A. As shown in FIG. 8A, after the inflammation was induced by treating the 3T3-L1 cells with LPS, the transcription factor having a significant activity for the AzA effect was FOXO, which is associated with a PI-3 Kinase/AKT pathway signaling pathway.

Figure 8B:
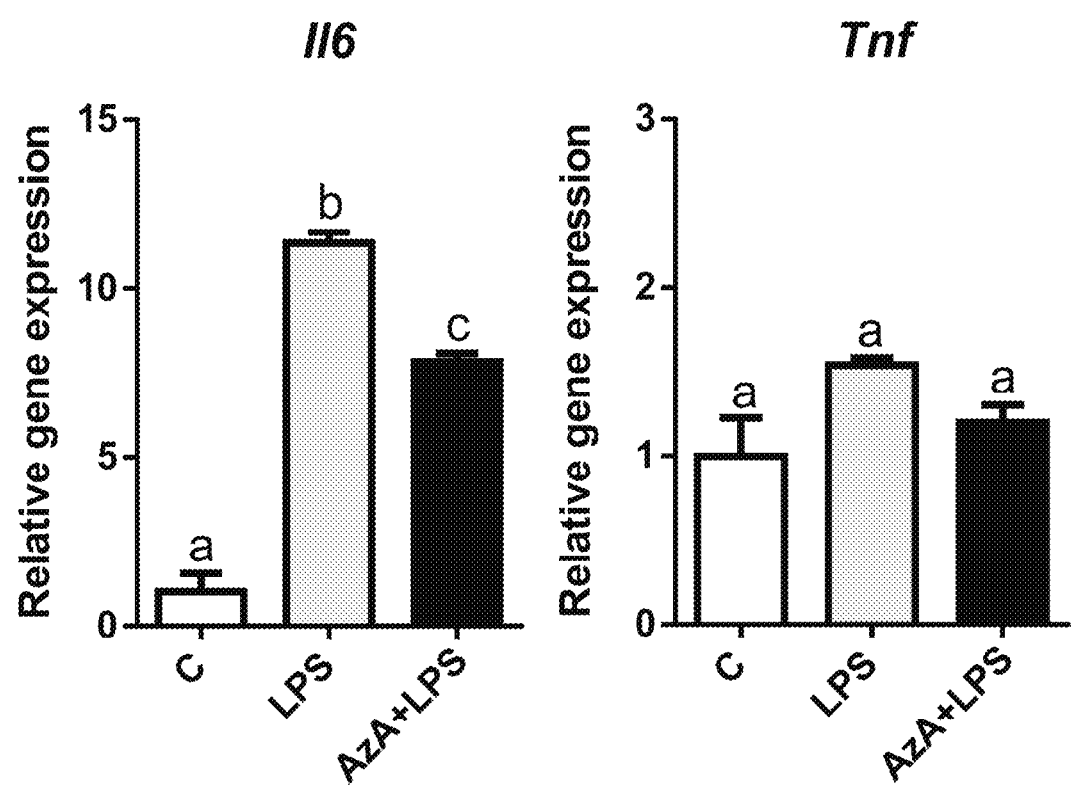

In addition, the results of measuring the gene expression of inflammatory response-mediated materials IL-6 and TNF-α in 3T3-L1 cells differentiated into adipose cells by the method described in Example 8-4 through qPCR were quantified, and are shown in FIG. 8B. As shown in FIG. 8B, it was confirmed that, IL-6 gene expression was significantly decreased in the AzA-treated group, compared with the control group. The result shows that the AzA exhibits an anti-inflammatory effect by reducing an LPS-induced IL-6 inflammation factor.

Example 9. Confirmation of LPS-Induced Inflammation Inhibitory Effect by an AzA in LPS Mouse 9-1) Experimental Animal Model Eight-week-old C57BL/6J male rats were purchased from Samtako (Gyeonggi-do, Korea). All experiments were carried out according to protocols approved by the Animal Experiment Committee of Korea University (Protocol No. KUIACUC-20090420-4). Mice were maintained under a 12-hour photoperiod at 21 to 25° C. and relative humidity of 50% to 60%. In normal groups and LPS-induced groups, 100 μL of deionized water was administered to each mouse using an oral sonde for 4 days, and 100 μL of LPS was intraperitoneally injected at a dose of 10 mg/kg one hour after the administration with deionized water on the last day, Day 4. In a group into which LPS was administered after the AzA administration, each mouse was orally administered 100 μL of AzA at a dose of 100 mg/kg for 4 days, and intraperitoneally injected with 100 μL of 10 mg/kg LPS one hour after the AzA administration on the last day, Day 4. Sixteen hours after the LPS intraperitoneal injection, the mice were anesthetized with avertin, and dissected to extract liver tissue. The liver tissue was obtained, immediately stored in liquid nitrogen, and then stored at −80° C.

9-2) cDNA Synthesis

1 μg of RNA extracted from the stored liver tissue was used to synthesize cDNA using a ReverTra Ace® qPCR RT kit (TOYOBO, Osaka, Japan). More specifically, to increase the reaction efficiency of RT-PCR, the extracted RNA was treated at 65° C. for 5 minutes, and then immediately stored on ice. Subsequently, a total of 8 μL of a reaction mixture was prepared with 2 μL of a 4×DNA Master Mix containing a gDNA remover, 0.5 μg of RNA and distilled water (nuclease-free water), and reacted at 37° C. for 5 minutes. Subsequently, a 5×RT Master mix was added to the reaction mixture, reacted at 37° C.-5 min, 50° C.-5 min and 98° C.-5 min to synthesize cDNA.

9-3) Quantitative Real-Time PCR (qPCR)

The cDNA synthesized by the above method was subjected to qPCR using a THUNDERBIRD SYBR qPCR Mix (TOYOBO, Osaka, Japan) and an iQ5 iCycler system (Bio-Rad, California, USA). More specifically, amplification was performed with initial denaturation at 95° C. for 4.5 minutes, and for 40 cycles of additional denaturation at the same temperature for 10 seconds, annealing and cooling at 55 to 60° C. for 30 seconds, and elongation at 68° C. for 20 seconds. The degree of the expression of each gene was standardized using GAPDH expression. Primers were designed using the Nucleotide BLAST software of the National Center for Biotechnology Information (NCBI), and purchased from Bionics (Seoul, Korea).

9-4) Statistical Analysis

For statistical analysis, a significance test between two groups was performed using a Student's t-test, and when $P<0.05$, the groups have significance, compared with the control group (*: $P<0.05$, : $P<0.01$, *: $P<0.001$). The significance test between two or more groups used one-way ANOVA, and the error bars of each graph are expressed as mean±SEM.

Figure 9:
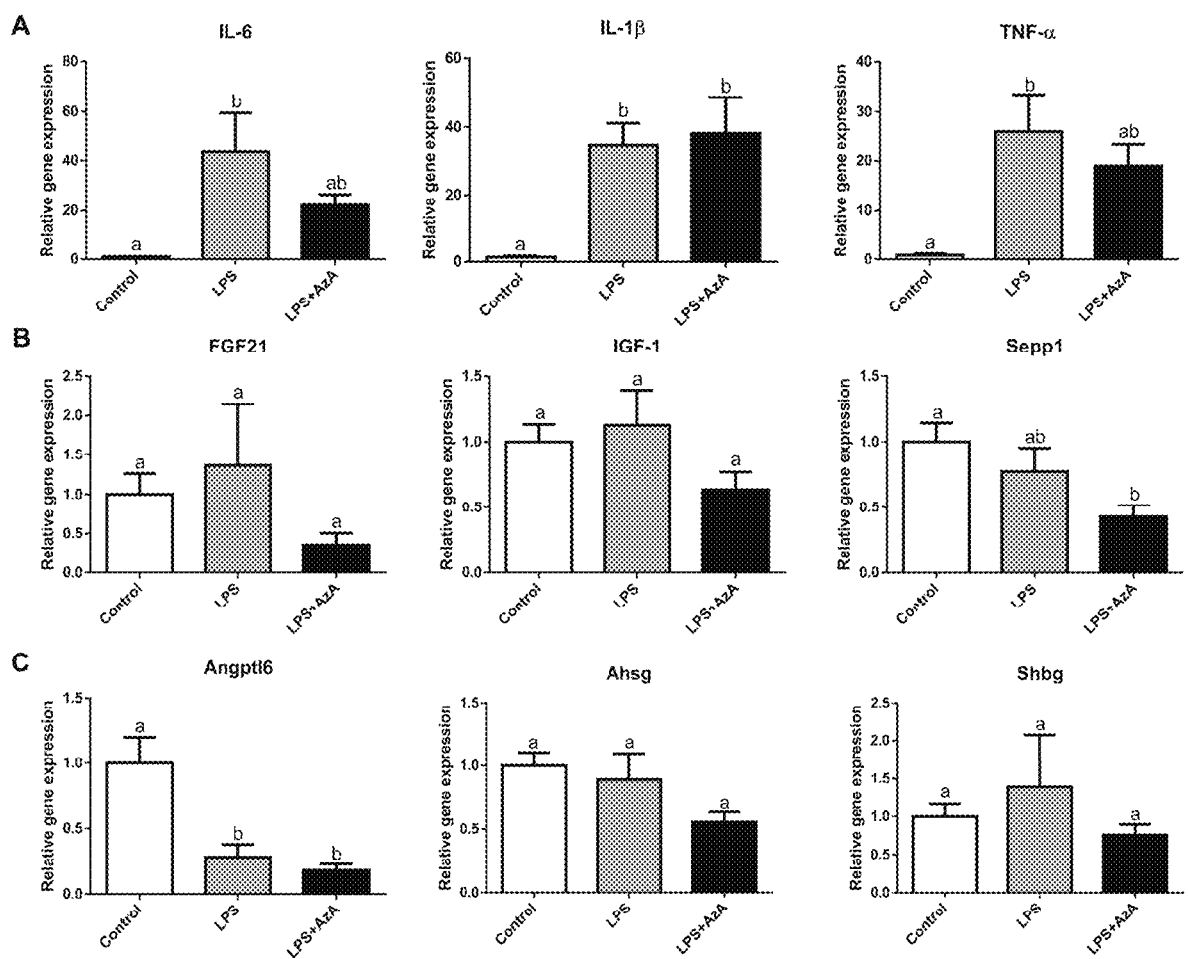
FIG. 9 shows the change in gene expression levels by LPS injection after the AzA is injected into C57BL/6J male mice for 3 days. Specifically, A shows a set of graphs analyzing gene expression levels of inflammation markers, B shows a set of graphs analyzing gene expression levels of growth factors, and C and D show a set of graphs analyzing gene expression levels of hepatokines.

9-5) Confirmation of LPS-Induced Inflammation Inhibitory Effect of an AzA in Mouse To investigate the effect of an AzA on in vivo inflammation of a mouse in Example 9-1, the AzA was intraperitoneally injected into a C57BL/6J male mouse for 3 days, LPS was injected thereinto, and then expression levels of inflammatory cytokines, hepatokines, growth factors and inflammatory marker genes were analyzed by the methods described in Examples 9-2 and 9-3. As a result, as shown in FIG. 9, A shows the gene expression levels of inflammatory cytokines IL-6 and TNF-α, and a tendency of reduction in inflammatory responses by the AzA after inflammation is induced by LPS. A shows the gene expression levels of inflammatory markers, B shows the gene expression levels of growth factors, and C and D show the gene expression levels of hepatokines.

It should be understood by those of ordinary skill in the art that the above description of the present disclosure is exemplary, and the exemplary embodiments disclosed herein can be easily modified into other specific forms without departing from the technical spirit or essential features of the claimed invention. Therefore, the exemplary embodiments described above should be interpreted as illustrative and not limited in any aspect. Therefore, the scope of the disclosure is defined not by the exemplary embodiments described above, but by the claims and their equivalents, and all variations within the scope of the claims and their equivalents are to be construed as being included in the disclosure.

The invention claimed is:

1. A method for improving or treating fatty liver, which comprises:
administering an effective amount of an azelaic acid represented by the following Formula 1 or a pharmaceutically acceptable salt thereof to a subject:

[Formula 1]

HO—C(=O)—(CH2)7—C(=O)—OH;

and
confirming an activation of a receptor of the azelaic acid expressed in a liver tissue of the subject.

2. The method according to claim 1, wherein the fatty liver is non-alcoholic fatty liver.

3. The method according to claim 1, wherein the fatty liver is a steatohepatitis caused by deposition of a fat and inflammation in hepatocytes.

4. A method for improving or treating fatty liver, which comprises:
administering an effective amount of an azelaic acid represented by the following Formula 1 or a pharmaceutically acceptable salt thereof to a subject:

[Formula 1]

HO—C(=O)—(CH2)7—C(=O)—OH;

and
confirming an activation of a peroxisome proliferator-activated receptor α (PPARα) expressed in a liver tissue of the subject.

5. The method according to claim 4, wherein the fatty liver is non-alcoholic fatty liver.

6. The method according to claim 4, wherein the fatty liver is a steatohepatitis caused by deposition of a fat and inflammation in hepatocytes.

7. A method for improving or treating fatty liver, which comprises:

administering an effective amount of an azelaic acid represented by the following Formula 1 or a pharmaceutically acceptable salt thereof to a subject:

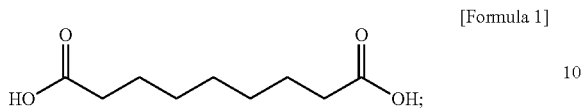

[Formula 1]

and confirming an inhibition of accumulation of triglycerides in a liver tissue of the subject.

8. The method according to claim 7, wherein the fatty liver is non-alcoholic fatty liver.

9. The method according to claim 7, wherein the method inhibits accumulation of triglycerides in the liver tissue by sequentially activating cAMP-PKA-CREB-PPARα through Olfr544 activation.

10. The method according to claim 7, wherein the fatty liver is a steatohepatitis caused by deposition of a fat and inflammation in hepatocytes.

* * * * *